(12) United States Patent
Nickel et al.

(10) Patent No.: US 10,842,793 B2
(45) Date of Patent: Nov. 24, 2020

(54) INHIBITORS OF THE UNCONVENTIONAL SECRETION OF FIBROBLAST GROWTH FACTOR 2 (FGF2) BY TUMOR CELLS AND USES THEREOF

(71) Applicants: Universität Heidelberg, Heidelberg (DE); European Molecular Biology Laboratory, Heidelberg (DE)

(72) Inventors: Walter Nickel, Schriesheim (DE); Joe Lewis, Dielheim (DE)

(73) Assignees: Universitat Heidelberg, Heidelberg (DE); European Molecular Biology Laboratory, Heidelberg (DE)

( * ) Notice: Subject to any disclaimer, the term of this patent is extended or adjusted under 35 U.S.C. 154(b) by 0 days.

(21) Appl. No.: 16/085,123

(22) PCT Filed: Feb. 7, 2017

(86) PCT No.: PCT/EP2017/000166
§ 371 (c)(1),
(2) Date: Sep. 14, 2018

(87) PCT Pub. No.: WO2017/167429
PCT Pub. Date: Oct. 5, 2017

(65) Prior Publication Data
US 2019/0307752 A1   Oct. 10, 2019

(30) Foreign Application Priority Data
Mar. 29, 2016 (GB) .................................. 1605173.2

(51) Int. Cl.
*A61K 31/519* (2006.01)
*A61K 31/437* (2006.01)
*C07D 471/04* (2006.01)

(52) U.S. Cl.
CPC .......... *A61K 31/519* (2013.01); *A61K 31/437* (2013.01); *C07D 471/04* (2013.01)

(58) Field of Classification Search
None
See application file for complete search history.

(56) References Cited

U.S. PATENT DOCUMENTS

2010/0063047 A1 * 3/2010 Borchardt .......... A61K 31/4365
514/234.2
2014/0275033 A1   9/2014 Li et al.

FOREIGN PATENT DOCUMENTS

EP   2626357 A1   8/2013
EP   2924038 A1   9/2015

OTHER PUBLICATIONS

Patent Cooperation Treaty, International Searching Authority, Search Report and Written Opinion for PCT/EP2017/000166, 11 pages, dated Apr. 20, 2017.
Sun, et al., "Design, Synthesis, and Evaluations of Substituted 3-[(3- or 4-Carboxyethylpyrrol-2-yl)methylidenyl] indolin-2-ones as Inhibitors of VEGF, FGF, and PDGF Receptor Tyrosine Kinases", J Med Chem 42, 5120-5130 (1999).

* cited by examiner

*Primary Examiner* — Samantha L Shterengarts
(74) *Attorney, Agent, or Firm* — Viksnins Harris Padys Malen LLP

(57) ABSTRACT

The present invention relates to compounds that have the capability of inhibiting the secretion of fibroblast growth factor 2 (FGF2) by tumor cells, as well as uses of said compound in medicine, in particular in the prevention and/or treatment of cancerous or inflammatory diseases.

9 Claims, 20 Drawing Sheets
Specification includes a Sequence Listing.

Figure 1:
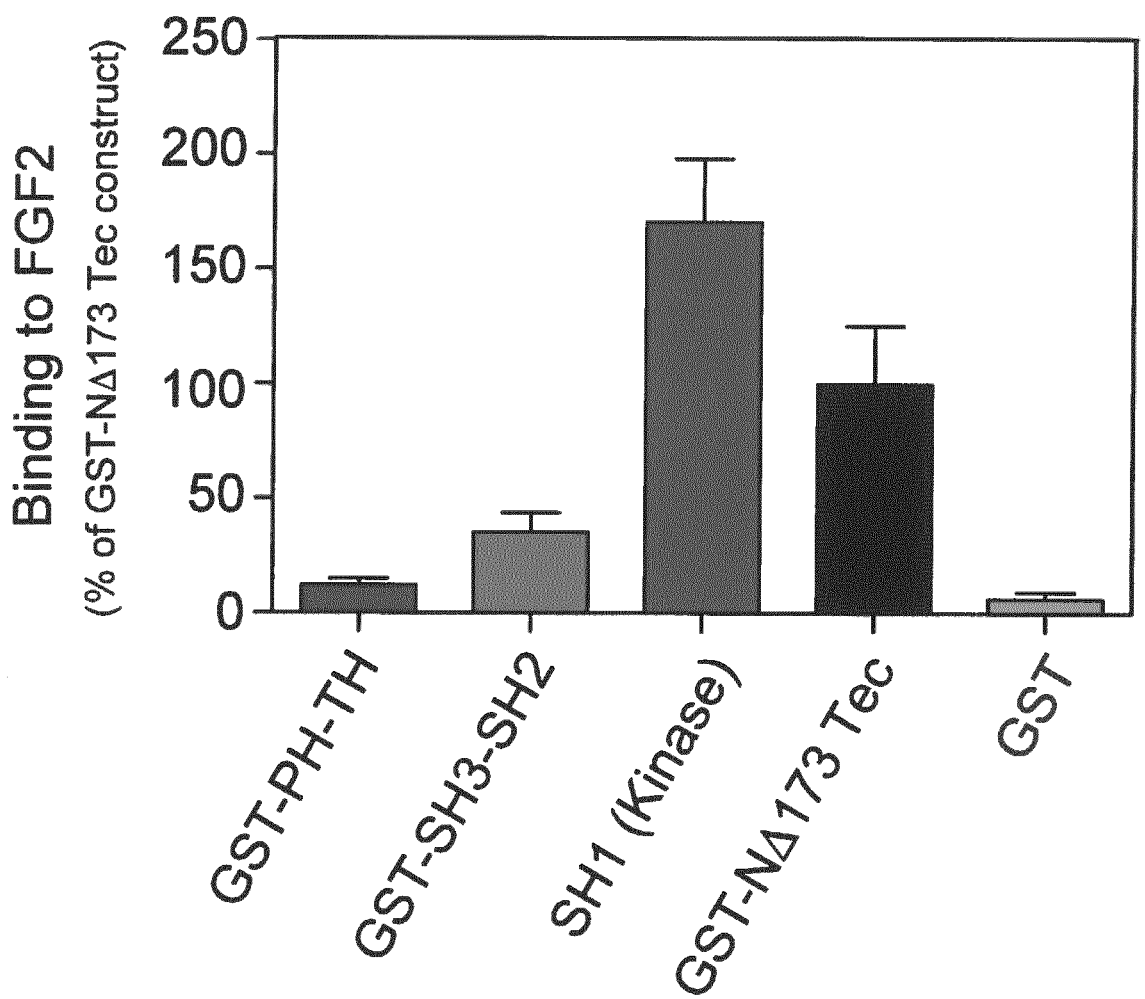

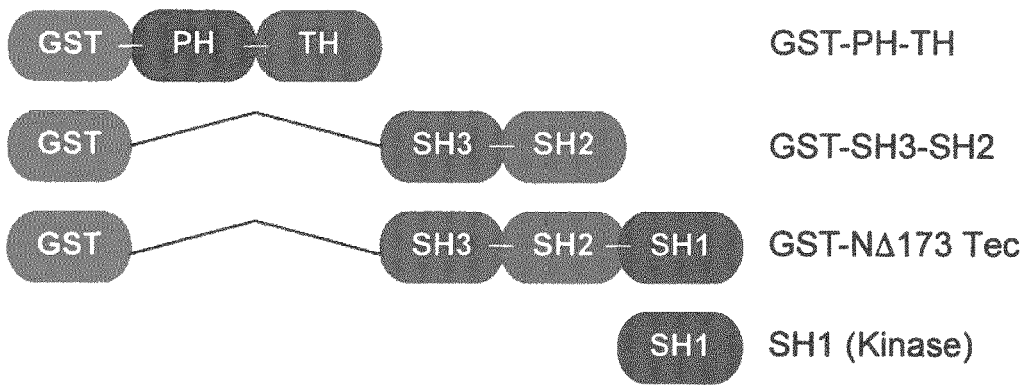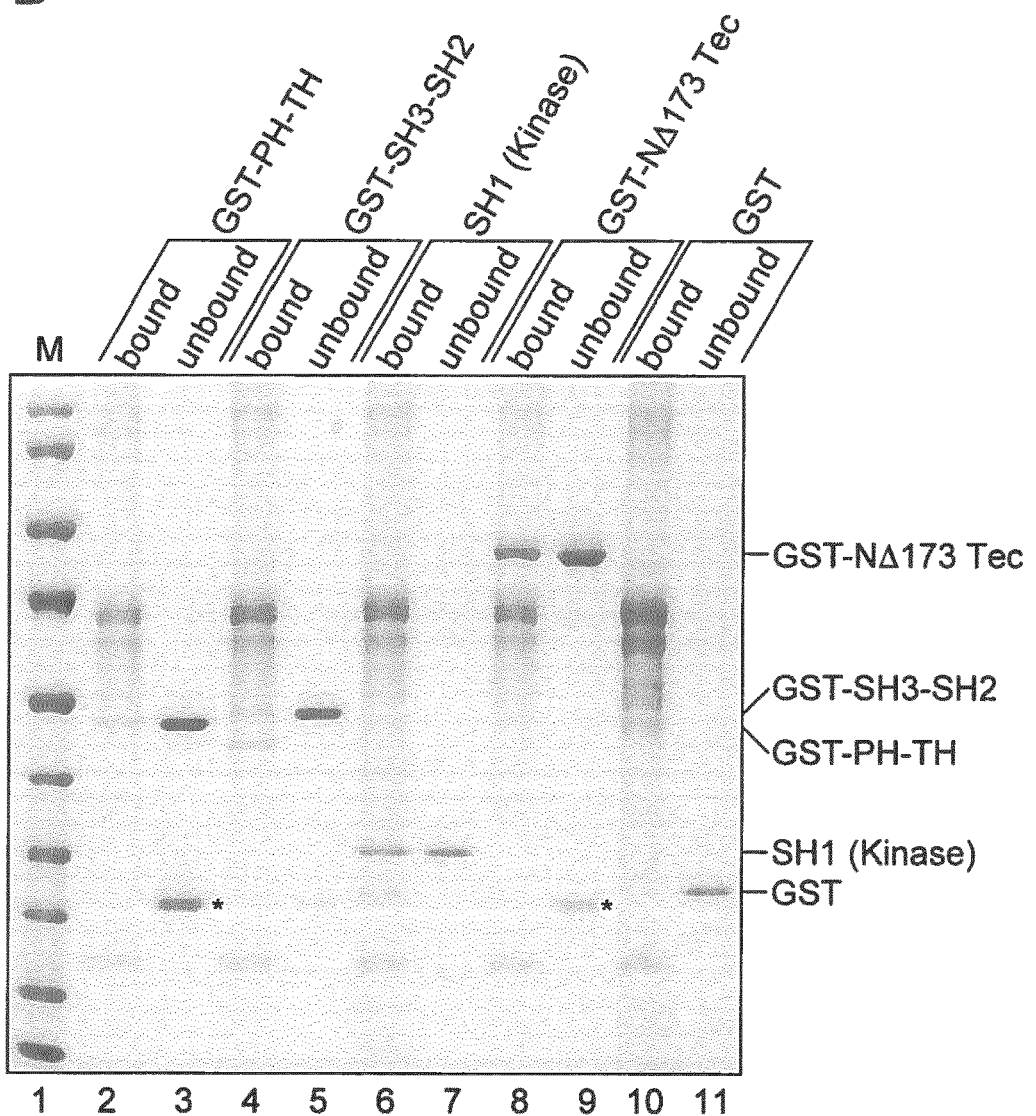
Figure 1 A, B

Figure 2:
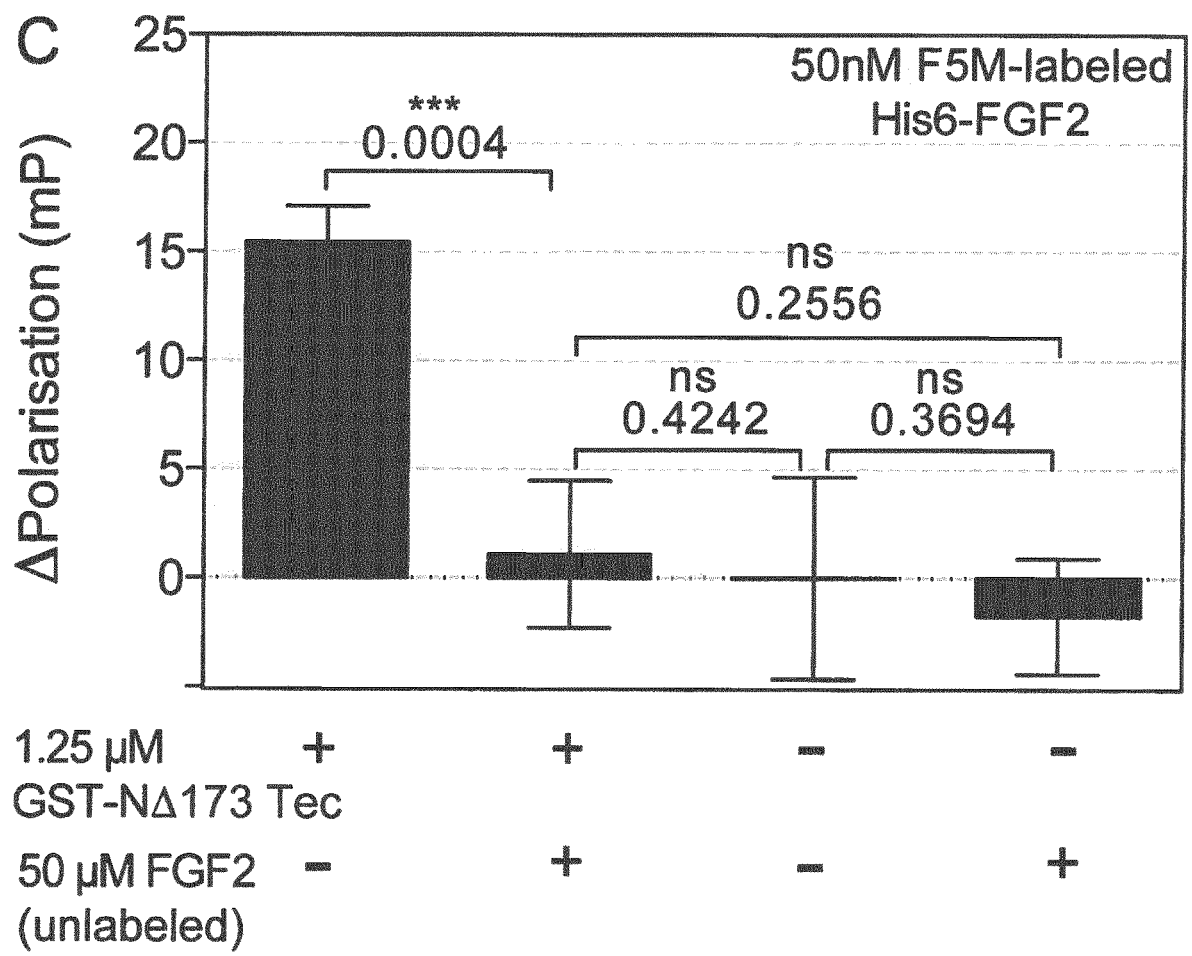

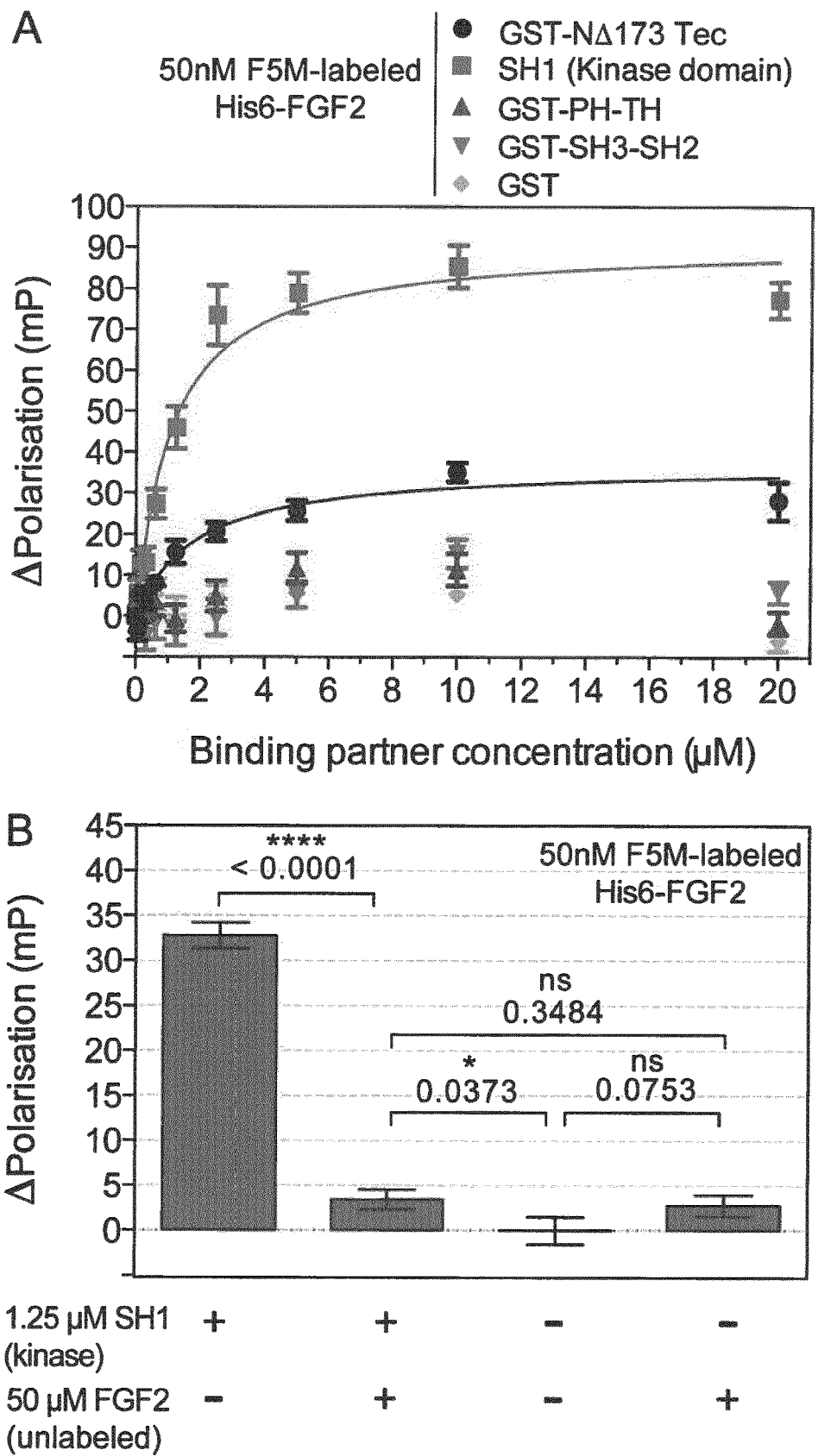
Figure 2 A, B

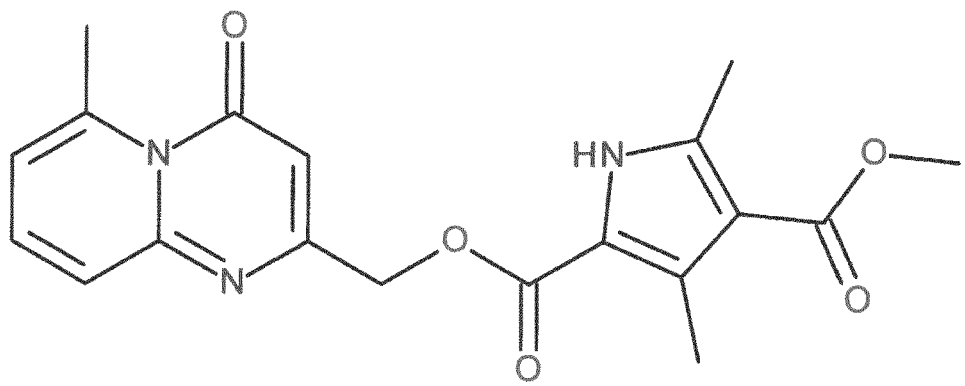
compound 6 (EMBL ID = 173026)
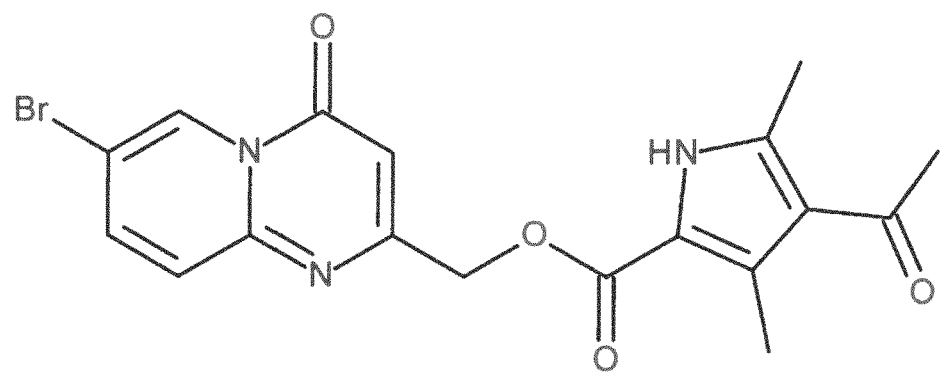
compound 14 (EMBL ID = 704930)
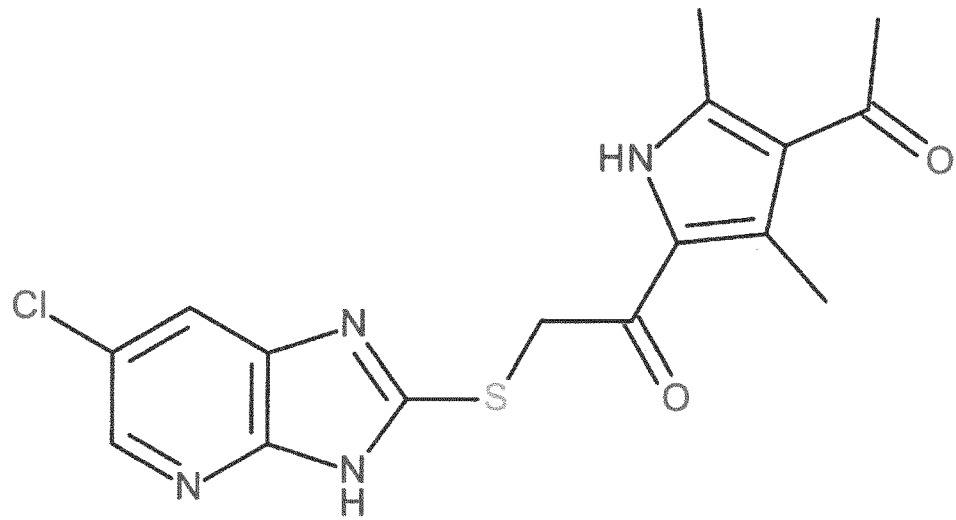
compound 21 (EMBL ID = 173078)
Figure 4

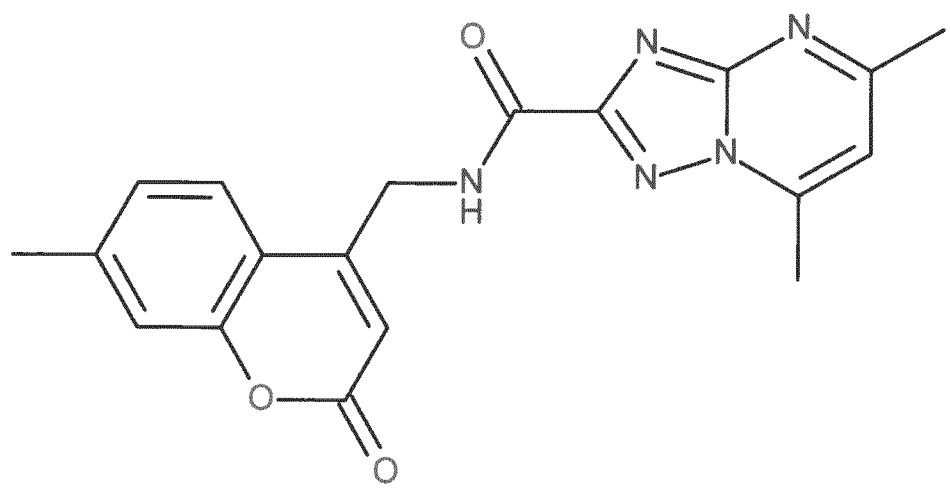
compound 18 (EMBL ID = 173059)
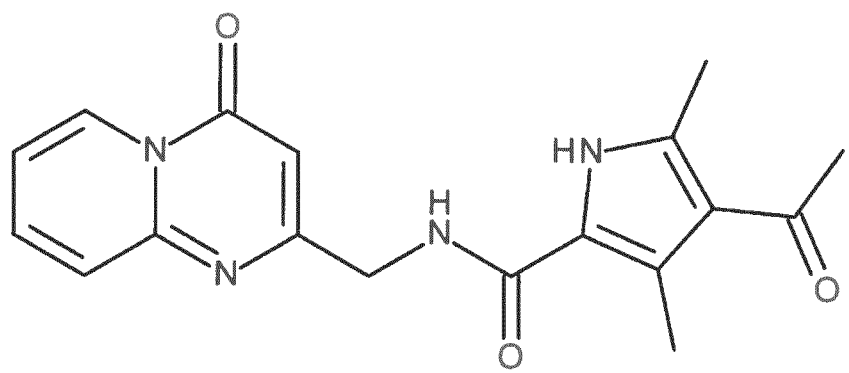
compound 19 (EMBL ID = 173060)
Figure 4 (cont.)

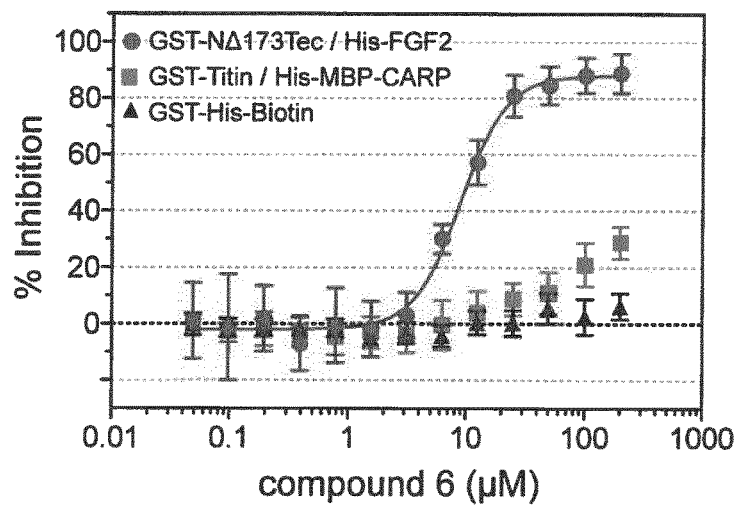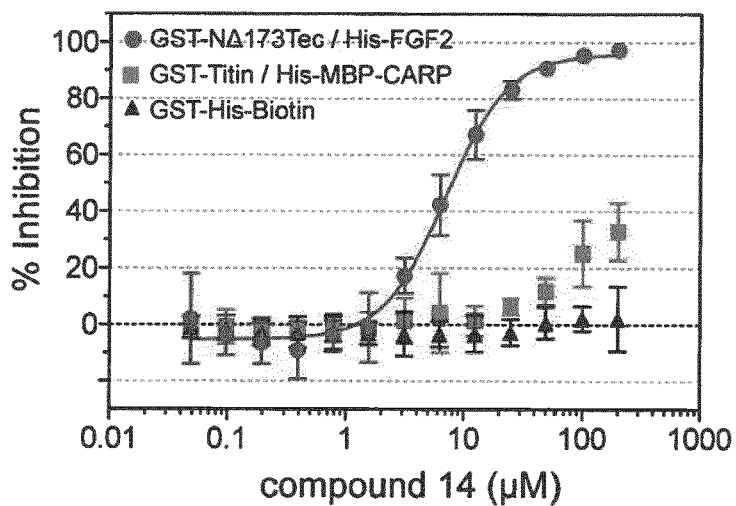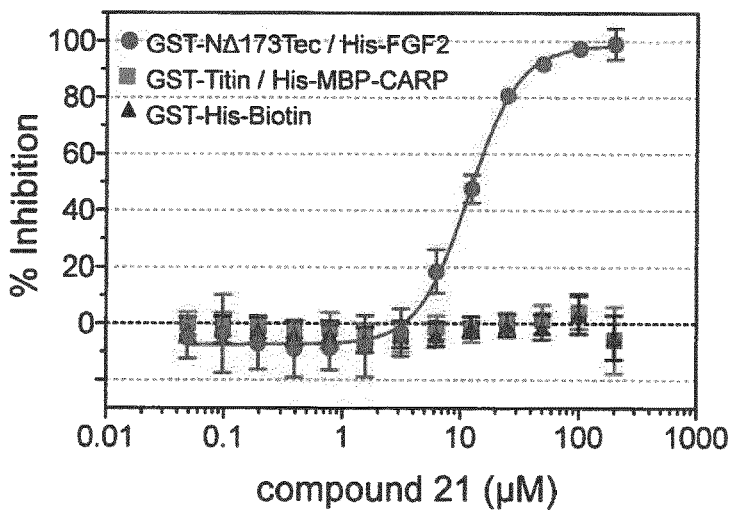
Figure 5 A, B, C

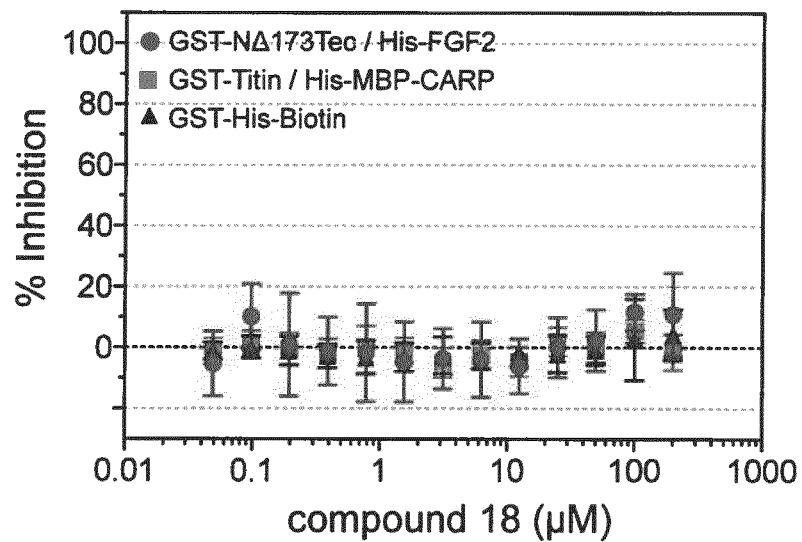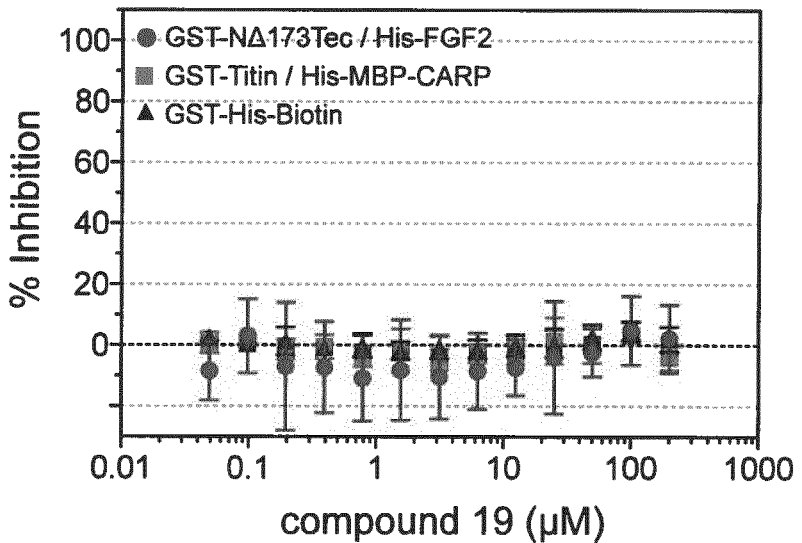
Figure 5 D, E

Figure 6:
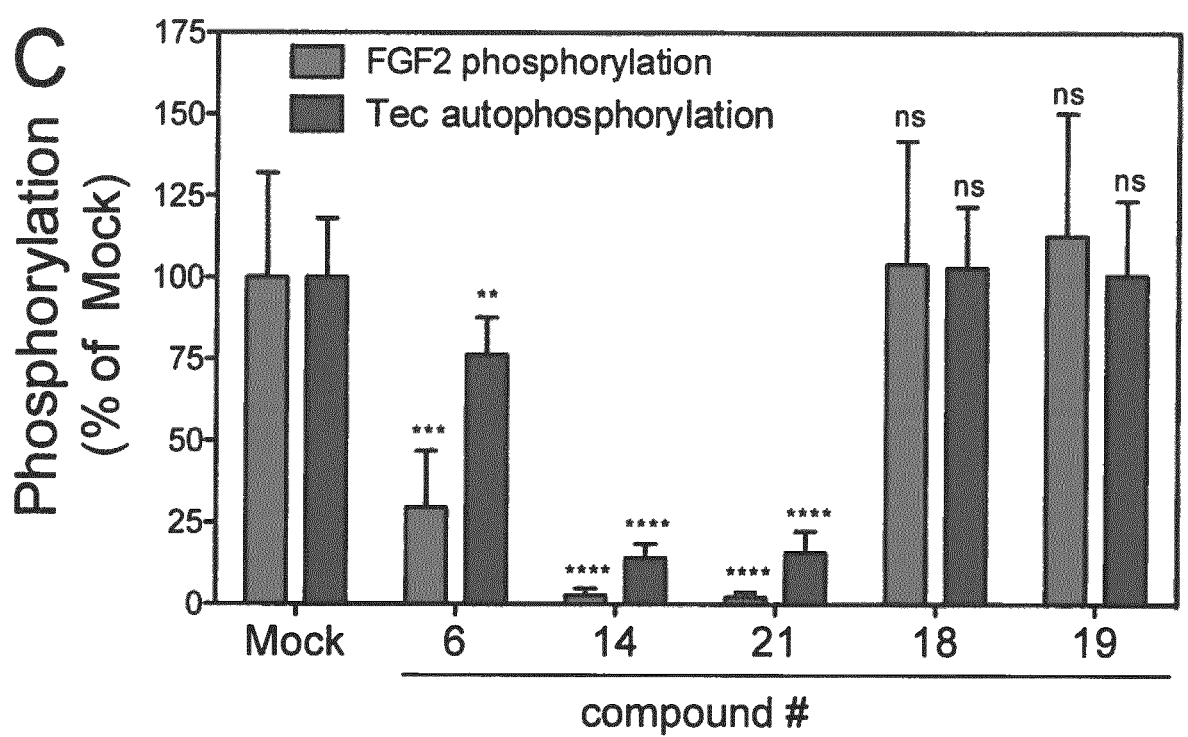

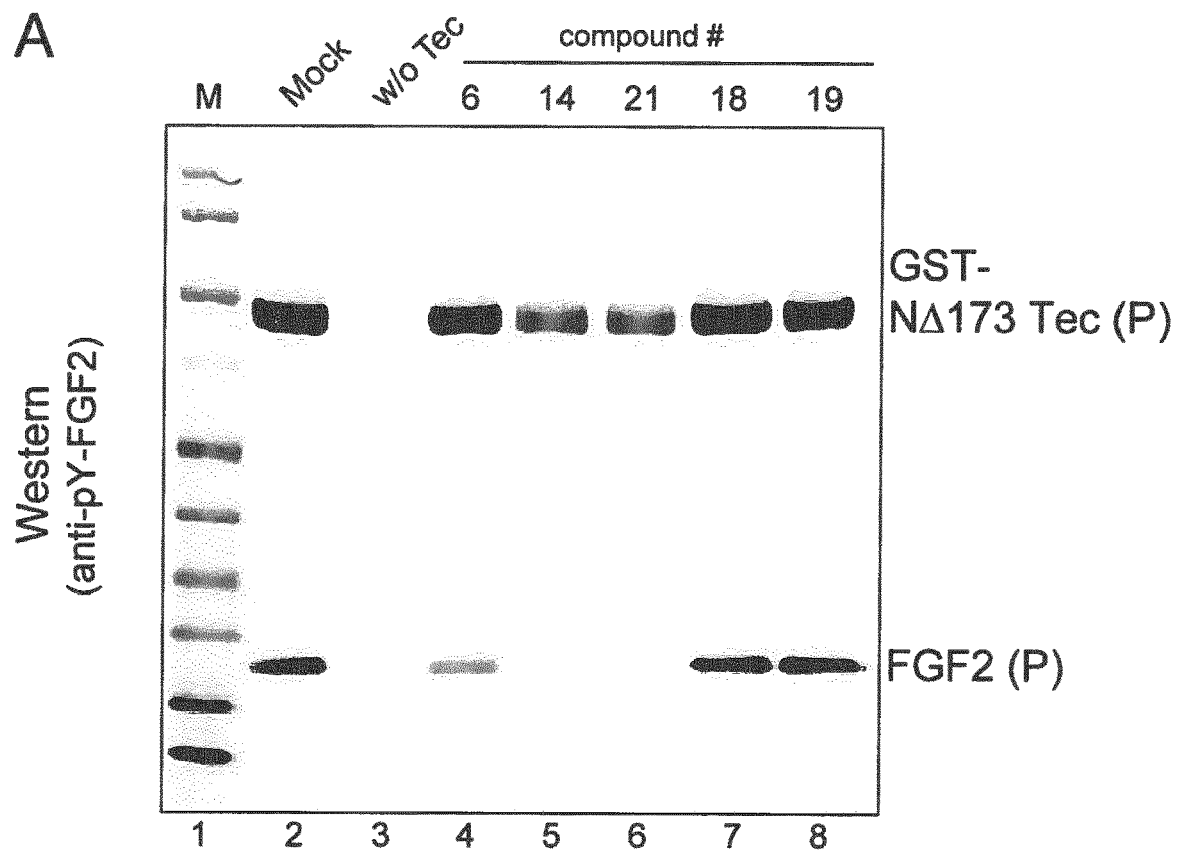
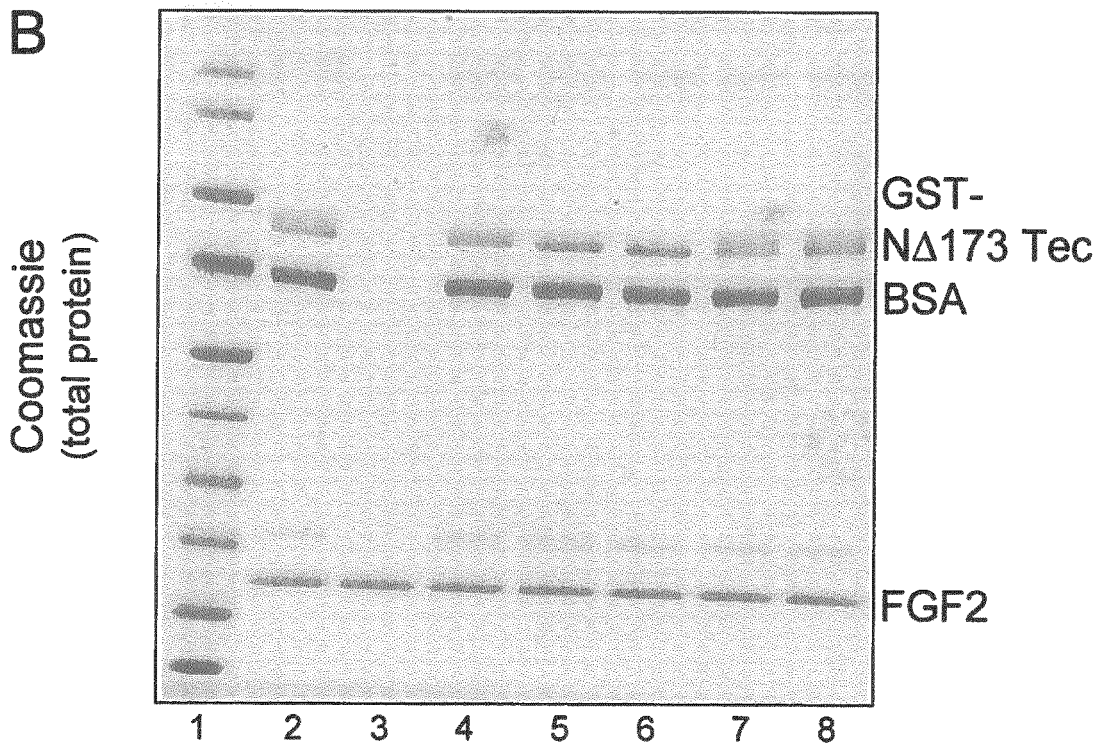
Figure 6 A, B

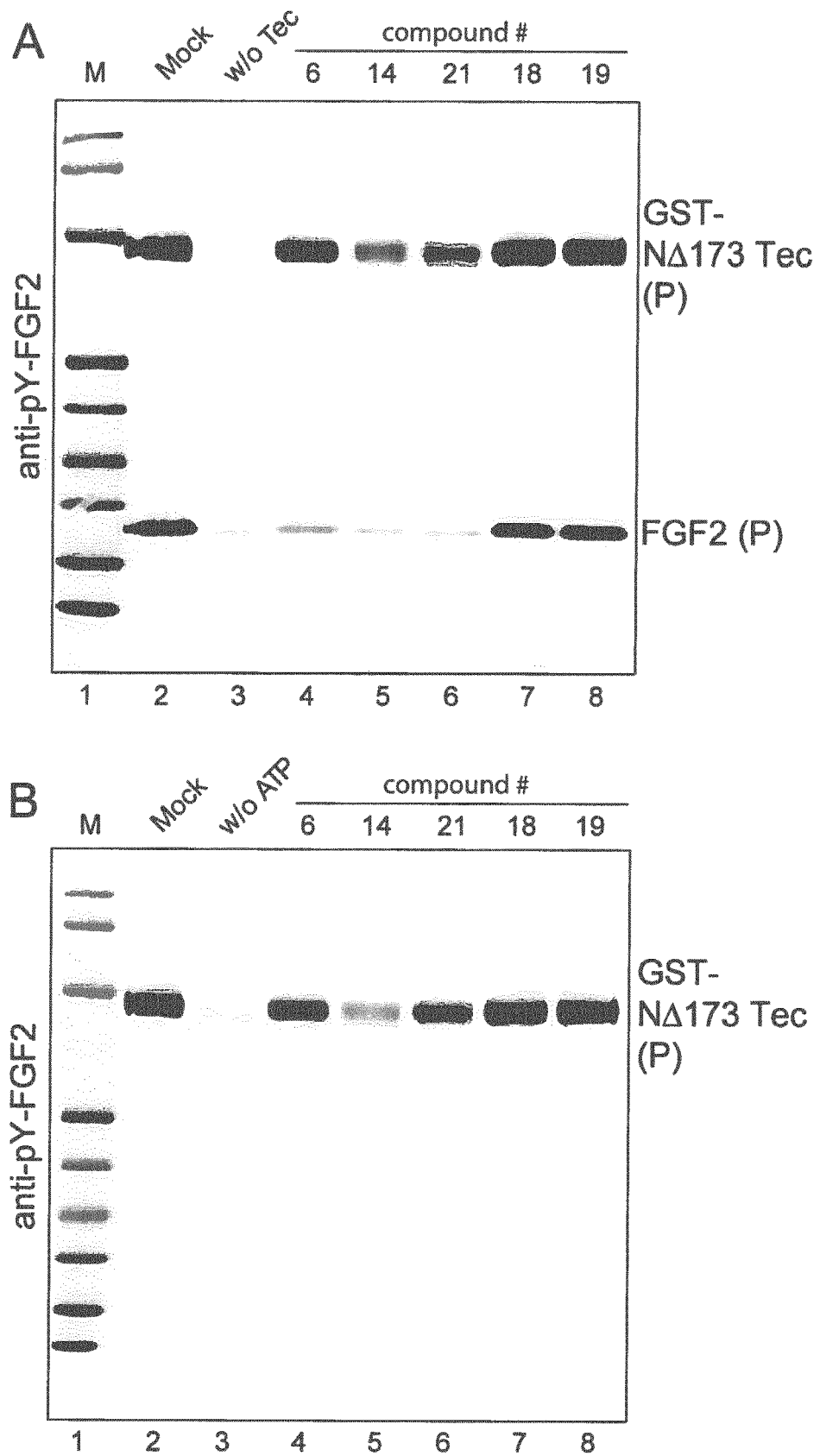
Figure 7 A, B

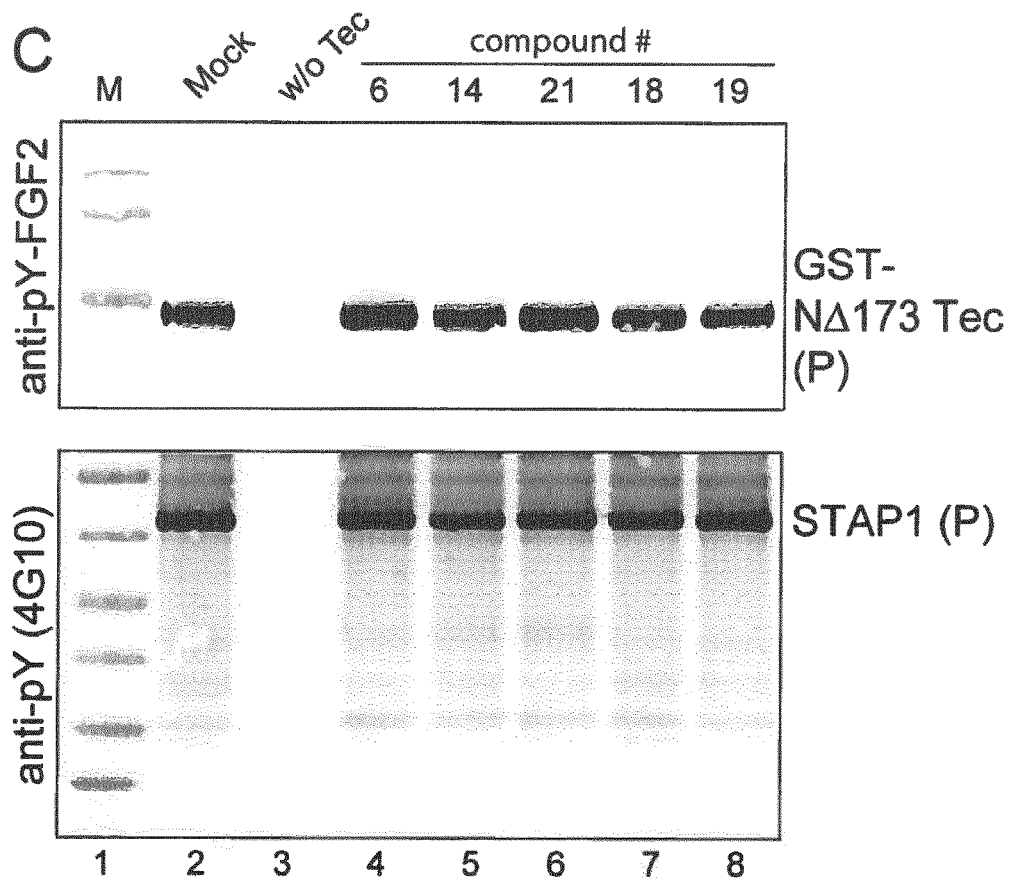
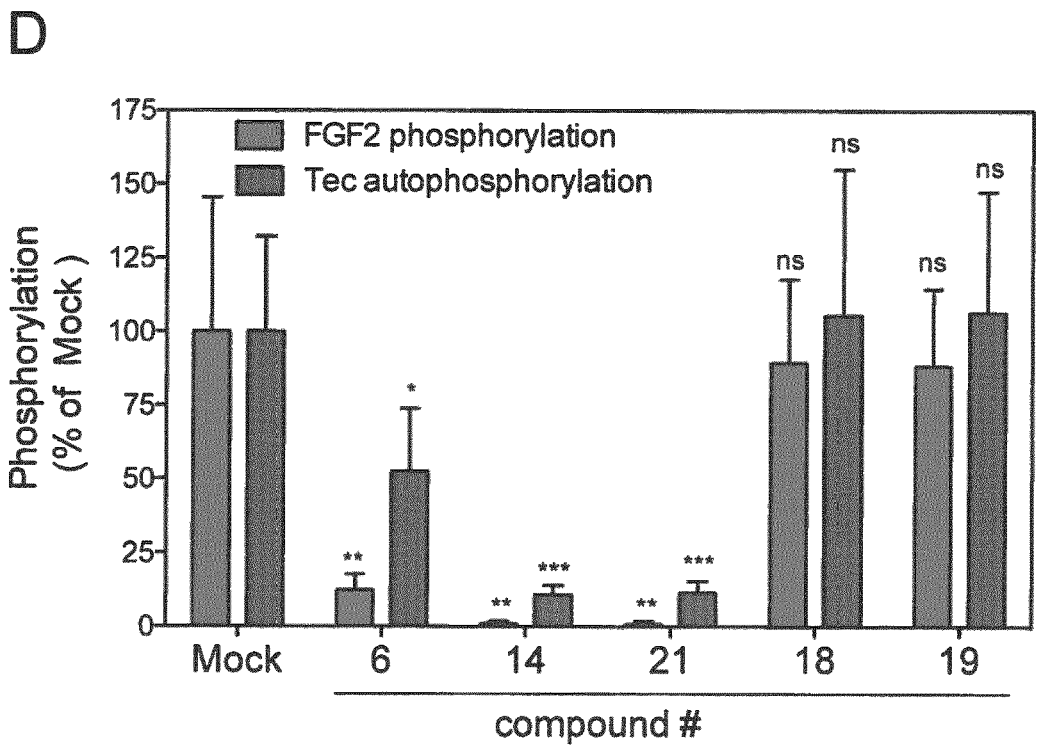
Figure 7 C, D

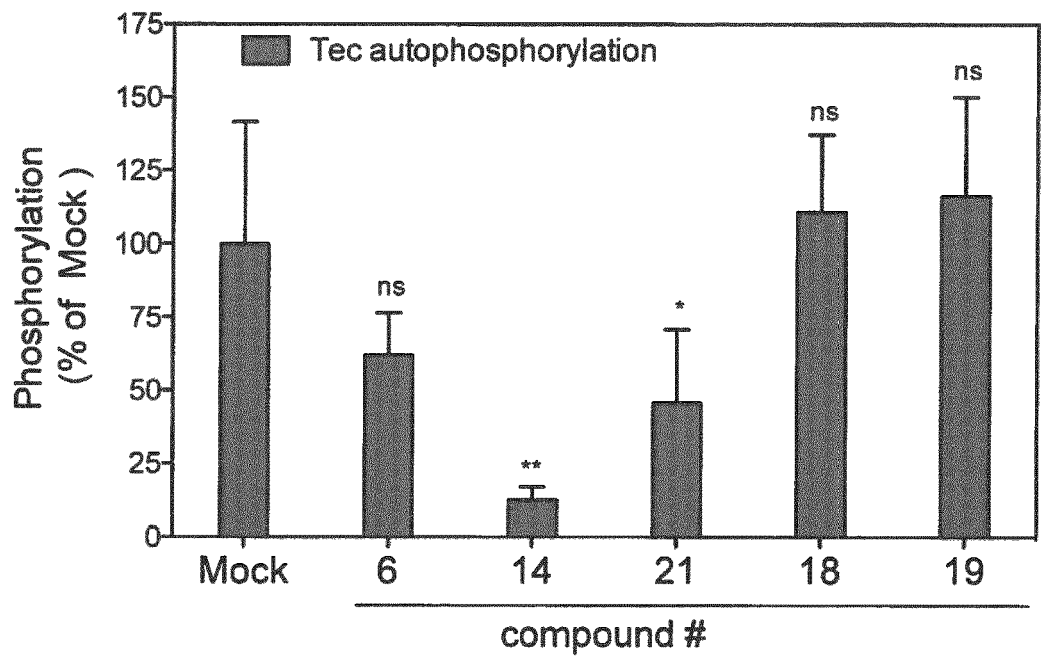
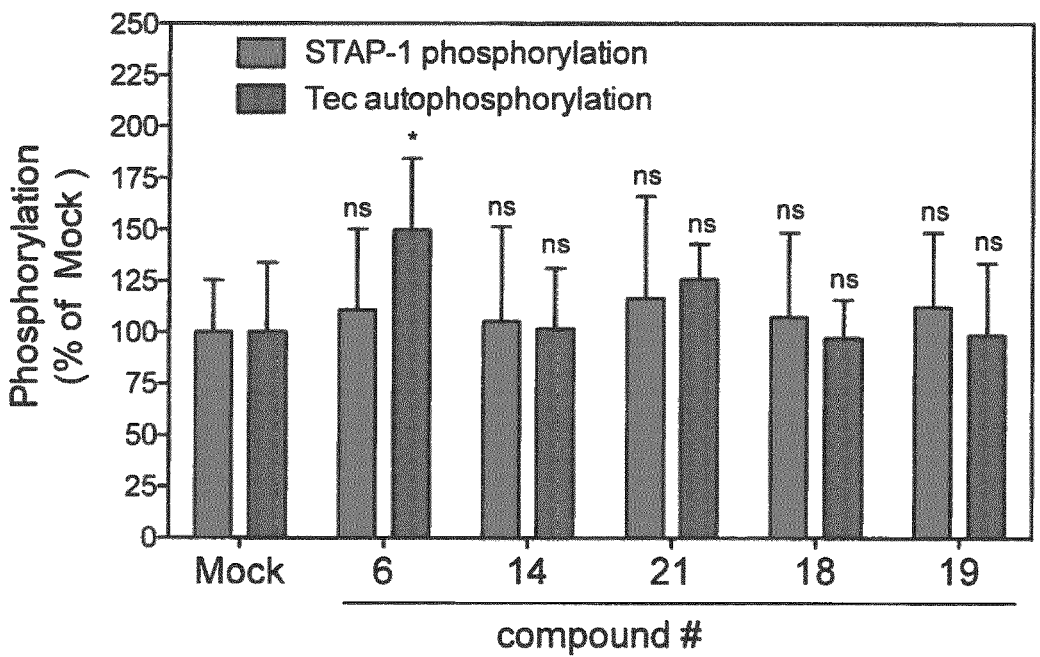
Figure 7 E, F

Figure 8:
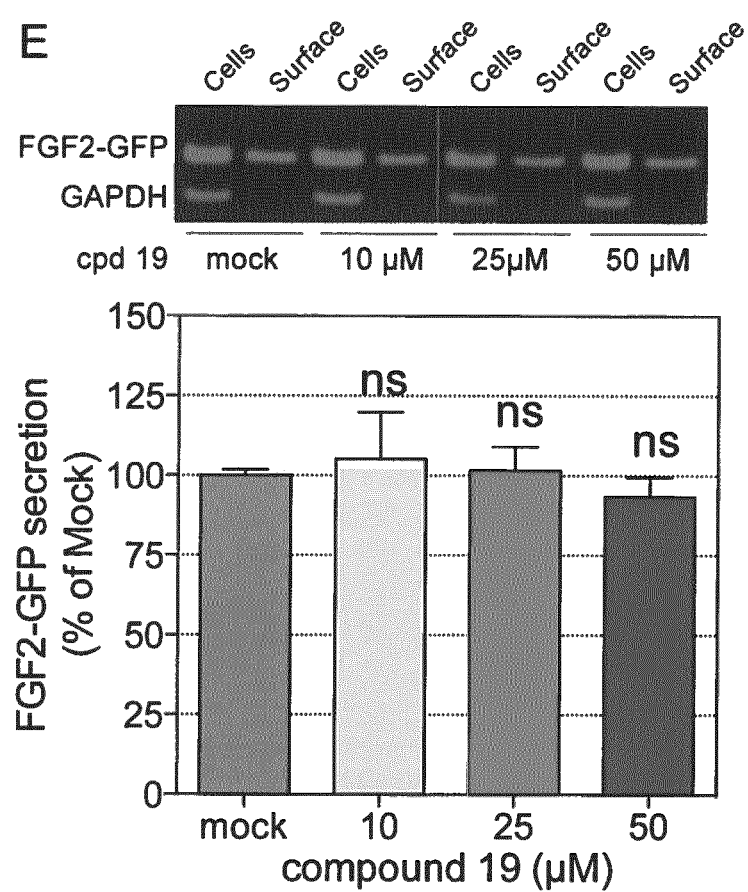

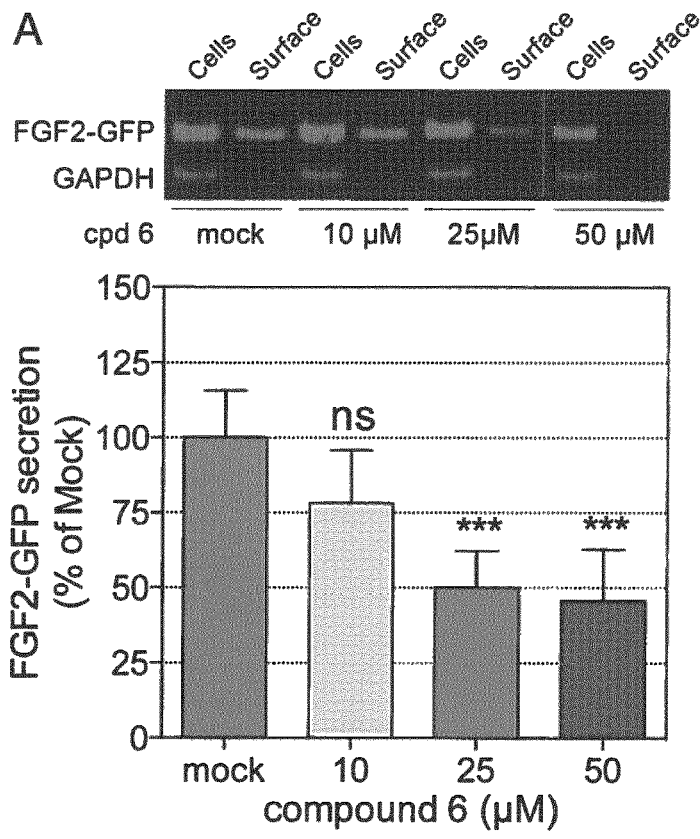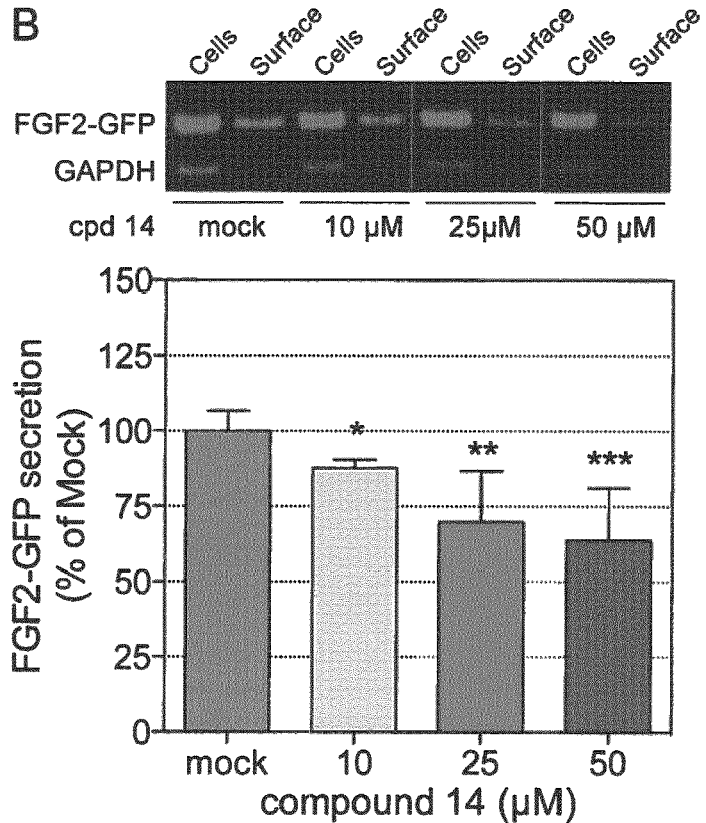
Figure 8 A, B

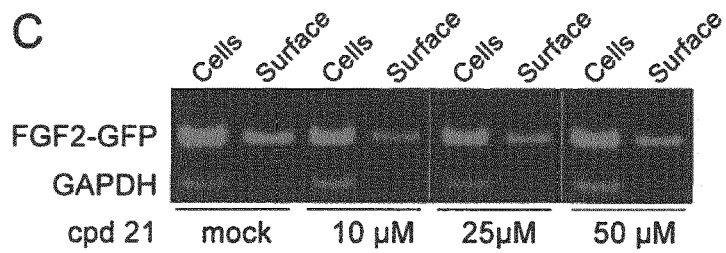
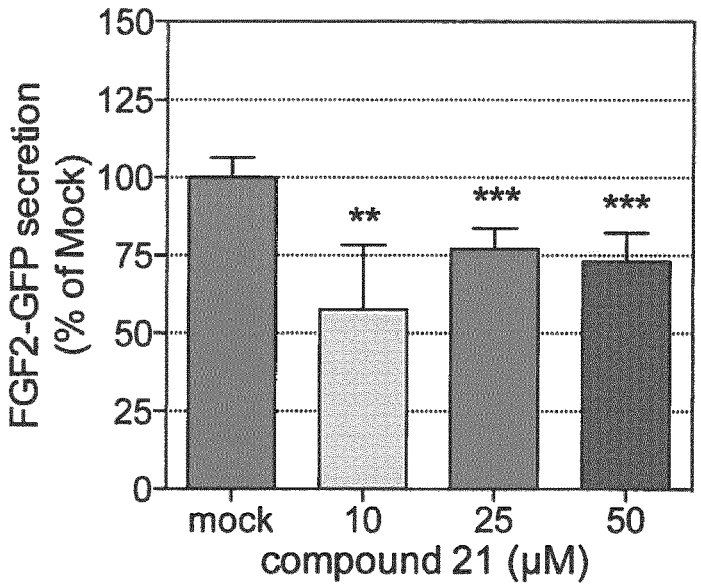
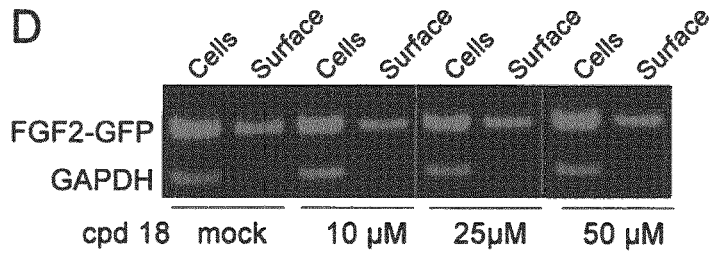
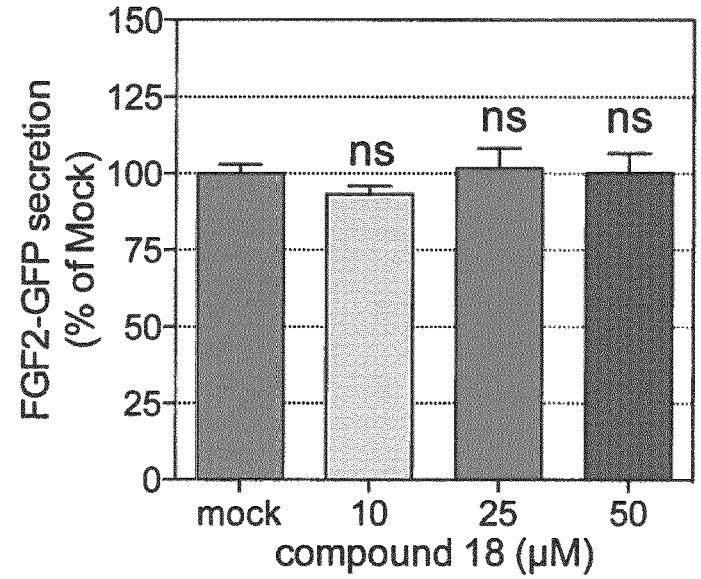
Figure 8 C, D

Figure 9:
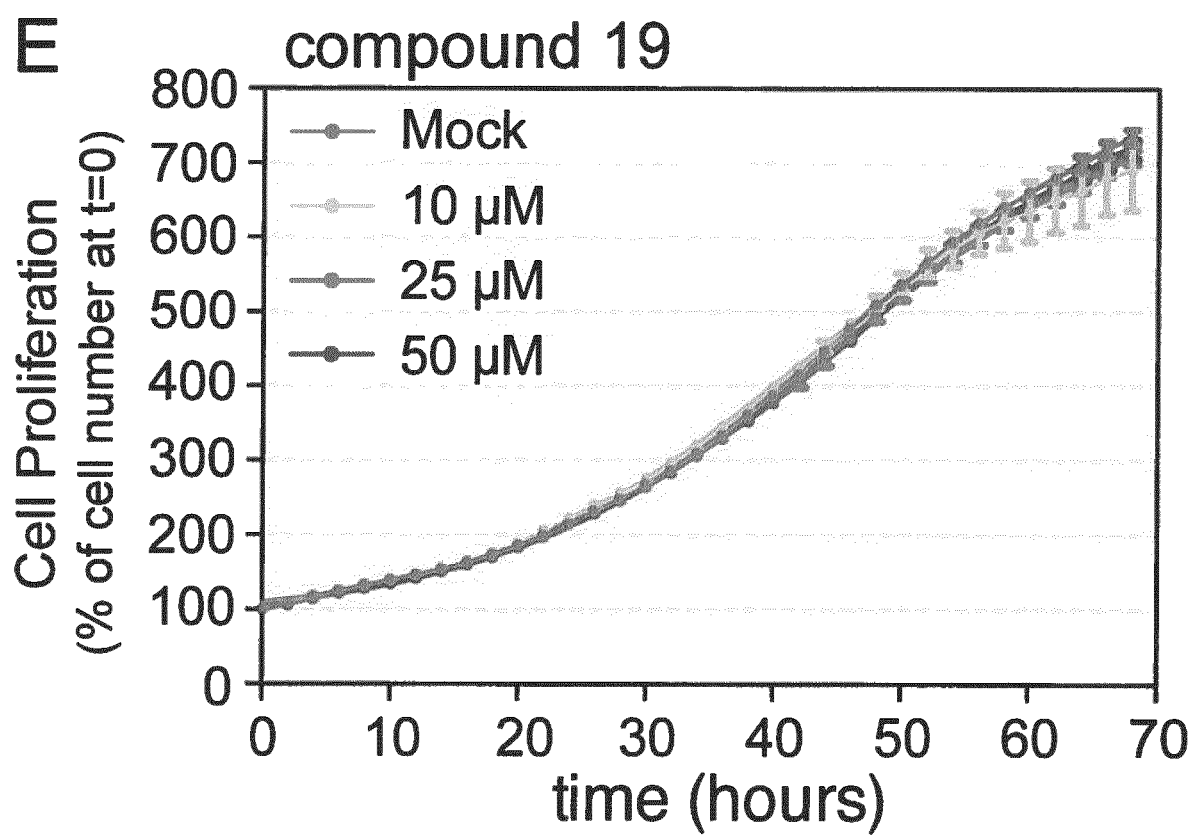

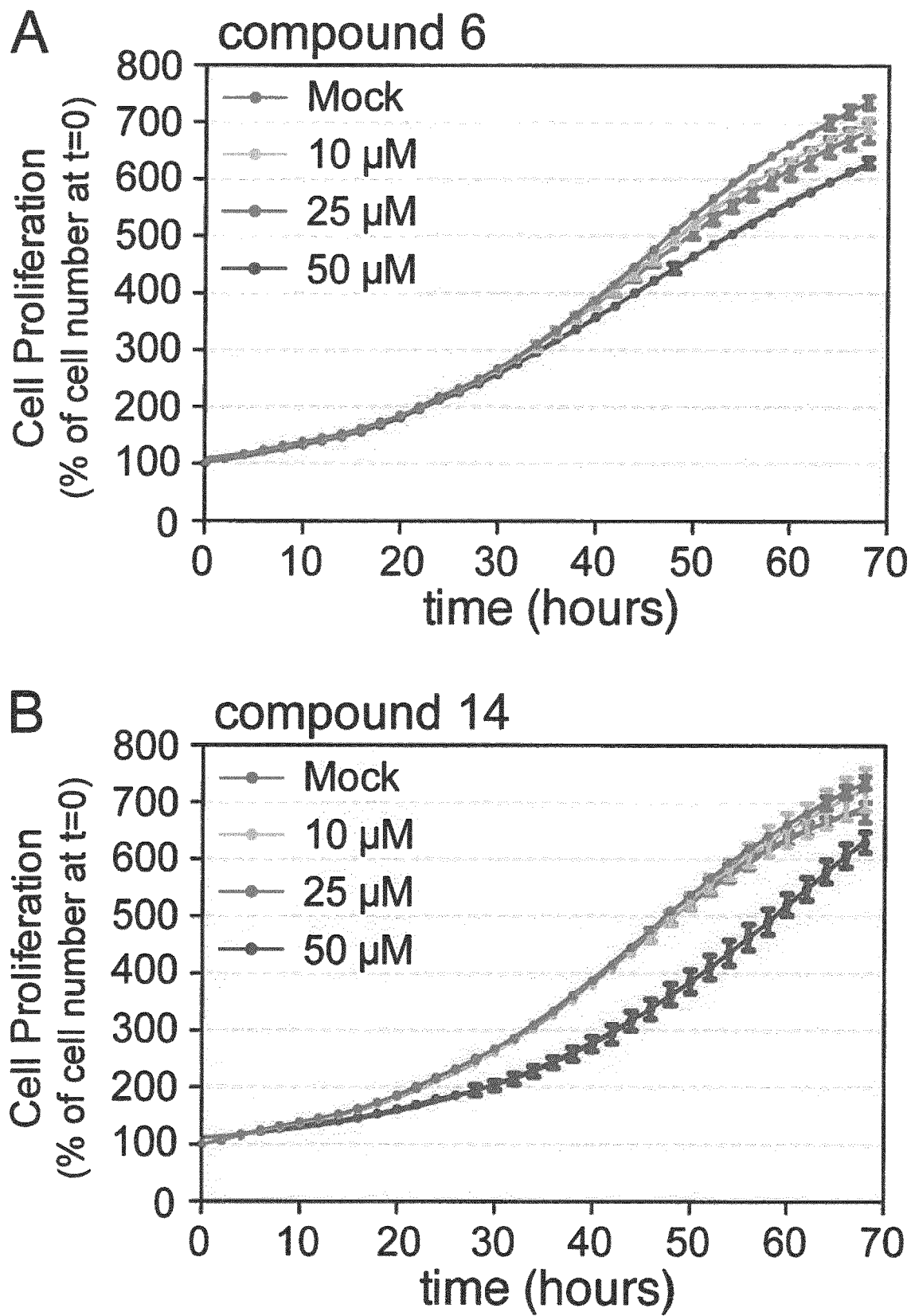
Figure 9 A, B

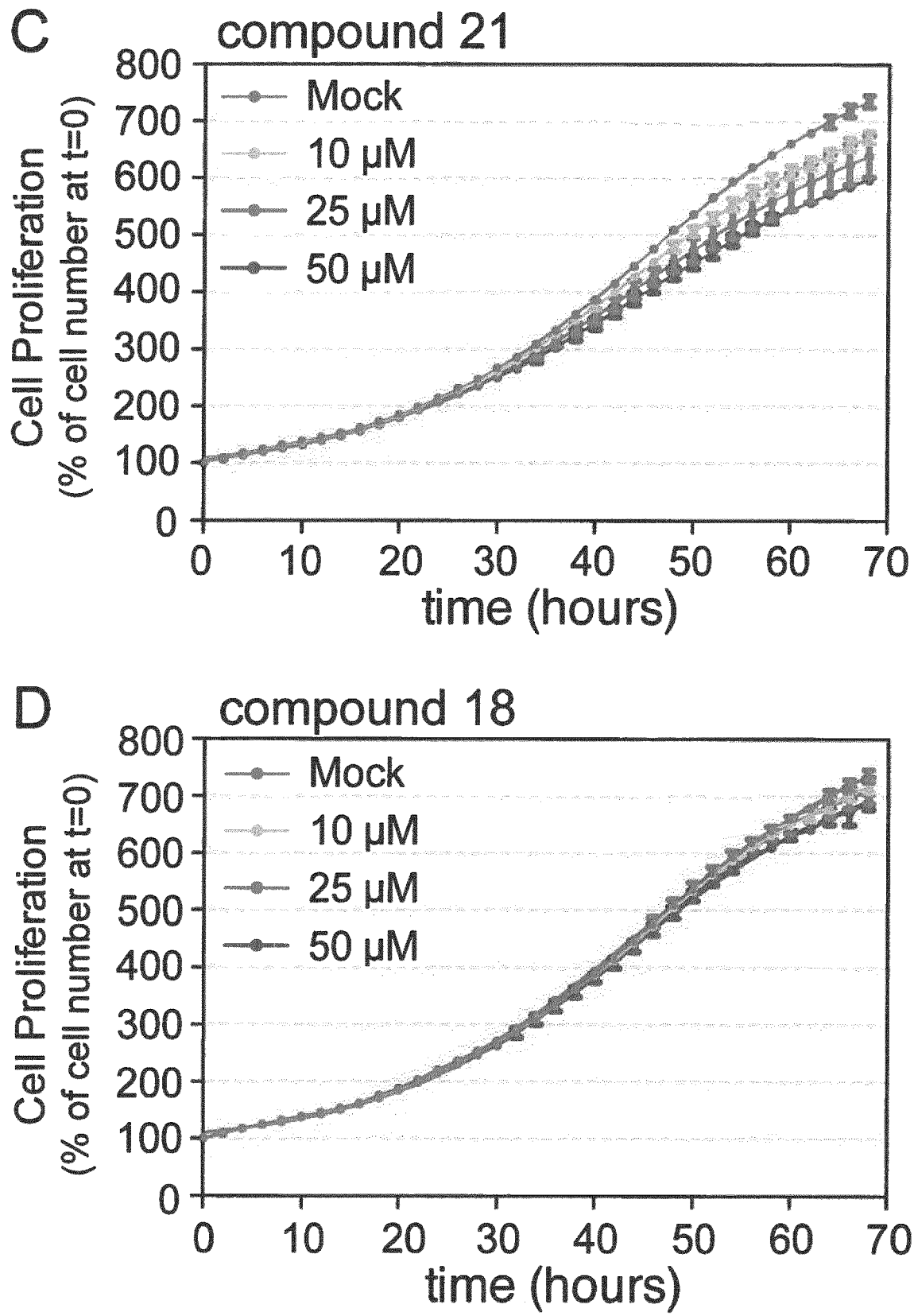
Figure 9 C, D

INHIBITORS OF THE UNCONVENTIONAL SECRETION OF FIBROBLAST GROWTH FACTOR 2 (FGF2) BY TUMOR CELLS AND USES THEREOF

CROSS-REFERENCE TO RELATED APPLICATION(S)

This patent application claims the benefit of priority of GB Application No. 1605173.2, filed Mar. 29, 2016.

SEQUENCE LISTING

The instant application contains a Sequence Listing which has been submitted in ASCII format via EFS-Web and is hereby incorporated by reference in its entirety. Said ASCII copy, created on Jan. 24, 2019, is named 08575_010US1_SL.txt and is 1,014 bytes in size.

The present invention relates to compounds that have the capability of inhibiting the secretion of fibroblast growth factor 2 (FGF2) by tumor cells, as well as uses of said compound in medicine, in particular in the prevention and/or treatment of cancerous or inflammatory diseases.

Fibroblast growth factor 2 (FGF2) is a potent mitogen promoting both tumor cell survival and tumor-induced angiogenesis. It is secreted by an unconventional secretory mechanism that is based upon direct translocation across the plasma membrane. Key steps of this process are (i) phosphoinositide dependent membrane recruitment, (ii) FGF2 oligomerization and membrane pore formation and (iii) extracellular trapping mediated by membrane proximal heparan sulfate proteoglycans. Efficient secretion of FGF2 is supported by Tec kinase that stimulates membrane pore formation based upon tyrosine phosphorylation of FGF2.

While the majority of secretory proteins carry signal peptides for endoplasmic reticulum (ER)/Golgi dependent secretion, a set of important growth factors and cytokines involved in tumor-induced angiogenesis and inflammatory responses is making use of alternative routes. These processes have collectively been termed 'unconventional protein secretion'. FGF2 and interleukin1β (IL1β) are prominent examples for secretory proteins that make use of such pathways. While the molecular mechanism by which IL1β is secreted from cells is debated and may differ in some aspects between various kinds of immune cells, the mechanism of the unconventional secretory pathway of FGF2 is emerging with great molecular detail. It is based upon direct translocation of folded species of FGF2 across plasma membranes. Hallmarks of this process are (i) FGF2 recruitment at the inner leaflet of the plasma membrane mediated by the phosphoinositide PI(4,5)P$_2$, (ii) FGF2 oligomerization and membrane pore formation and (iii) extracellular trapping of FGF2 mediated by membrane proximal heparan sulfate proteoglycans. In addition, based on a genome-wide RNAi screening approach, two factors physically associated with the plasma membrane have been identified to play a role in FGF2 secretion, Tec kinase and ATP1A1, the α subunit of the Na/K ATPase. While the precise role of ATP1A1 in FGF2 membrane translocation into the extracellular space is unknown, Tec kinase was shown to directly interact with FGF2 resulting in phosphorylation of tyrosine 81. It was further shown that a phosphomimetic variant form of FGF2 is secreted from cells in a Tec kinase independent manner. Furthermore, based upon biochemical reconstitution experiments, a phosphomimetic form of FGF2 was found to be characterized by an increased ability to form PI(4,5)P$_2$ dependent membrane pores, the intermediates of FGF2 membrane translocation in cells.

Tec kinase contains a pleckstrin homology (PH) domain mediating recruitment at the inner leaflet of plasma membranes in a PI(3,4,5)P$_3$ dependent manner. In a number of physiological settings, activation of various kinds of receptors causes PI(3,4,5)P$_3$ levels to increase. Under these conditions, Tec kinases are getting recruited to the inner leaflet of the plasma membrane. Tec kinase then becomes phosphorylated by plasma membrane resident Src kinases or by autophosphorylation within its activation loop resulting in enzymatic activation. In its activated state, Tec kinase phosphorylates target proteins. As FGF2 is a key signaling molecule in the context of many cancers, Tec kinase regulated secretion of FGF2 represents an interesting link to the up-regulation of PI3 kinases in many tumor cells. PI3 kinases catalyze the formation of PI(3,4,5)P$_3$ and high cellular levels of this phosphoinositide are likely to support efficient secretion of FGF2 which, in turn, promotes tumor cell proliferation.

In this context, the activity of FGF2 can be affected by receptor tyrosine kinases. However, these compounds have strong side effects. Further, many tumors rapidly develop resistance against said compounds.

Based on these considerations, the technical problem underlying the present invention is to provide inhibitors of the function of Tec kinase in the unconventional secretory pathway of FGF2 which could be used in the prevention and/or treatment of cancerous and inflammatory diseases.

The solution to the above technical problem is achieved by the embodiments characterized in the claims.

In particular, in a first aspect, the present invention relates to a compound according to Formula (I):

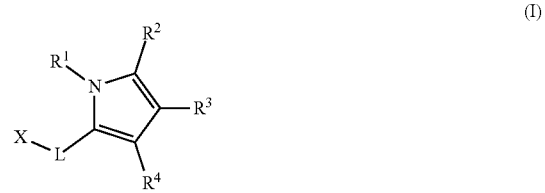

wherein
R$^1$, R$^2$ and R$^4$ are independently H or C$_1$-C$_3$ alkyl,
R$^3$ is —C(O)R$^5$, —C(O)OR$^5$, —CN or —CH$_2$OR$^5$,
L is a linker selected from the group consisting of —C(O)O—, —C(O)OCH$_2$—, and —C(O)CH$_2$S—,
X is an optionally substituted heterobicyclic group, and
R$^5$ is H or C$_1$-C$_3$ alkyl.

The above definitions of the linker moiety L are expressly intended to encompass both directional orientations, i.e., by way of example, the group —C(O)O— as defined herein, is intended to encompass both moieties

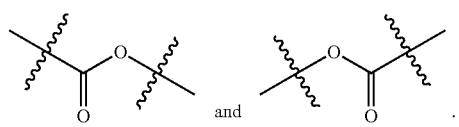 [SMILES: *OC(*)=O ; *OC(*)=O]

and

According to the present invention, group X is an optionally substituted heterobicyclic group, i.e., a heterocyclic group comprising two cycles and at least one heteroatom, wherein said cycles are independently 3- to 8-membered cycles and the at least one heteroatom is selected from the group consisting of N, O, and S. Preferably, the heteroatom is N.

In preferred embodiments, in Formula (I) of the present invention, $R^1$ is H, $R^2$ and $R^4$ are methyl, $R^3$ is —C(O)CH$_3$ or —C(O)OCH$_3$, L is —C(O)OCH$_2$— or —C(O)CH$_2$S—, and X is selected from the group consisting of

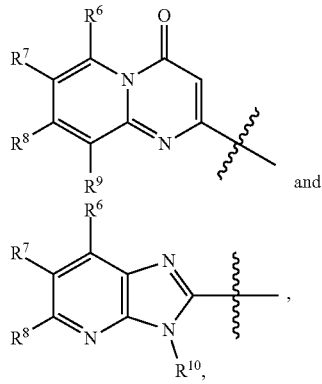
and wherein
$R^6$, $R^7$, $R^8$ and $R^9$ are independently H, halogen, $C_1$-$C_3$ alkyl, —CN, —CF$_3$, —OR$^{11}$ or Ar, and
$R^{10}$ and $R^{11}$ are independently H or $C_1$-$C_3$ alkyl.

The abbreviation "Ar" as used herein represents an aryl group.

More preferably, in Formula (I) of the present invention, X is selected from the group consisting of

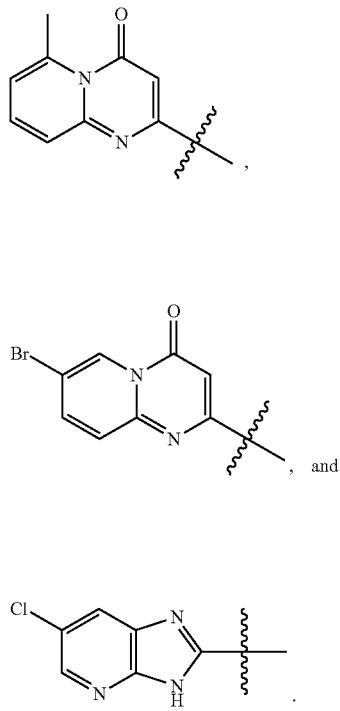

In a particularly preferred embodiment, the compound of the present invention is selected from the group consisting of Compounds 6, 14, and 21:

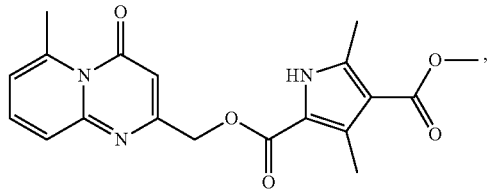
(Compound 6)

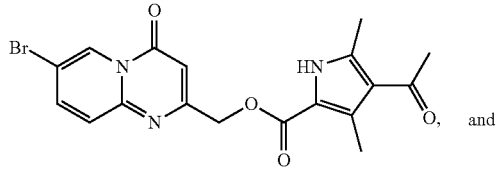
(Compound 14)

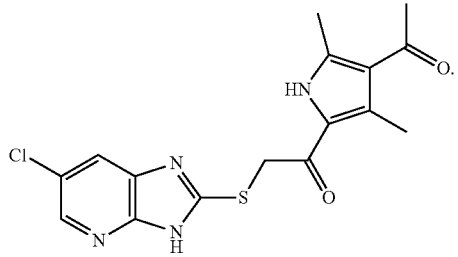
(Compound 21)

In another particular embodiment, the compound of the present invention is a compound according to Formula (I) as defined above, wherein said compound is not Compound 6, 14 or 21, as defined above.

According to the present invention, it is particularly preferred that the compound of the present invention as defined above is for use in medicine. More specifically, said compound can be for use in the prevention and/or treatment of a cancerous or inflammatory disease, wherein a cancerous disease is particularly preferred. In this context, a cancerous disease that can be prevented and/or treated according to the present invention includes any type of cancer wherein VEGF-mediated signaling occurs in tumor cells. Further, an inflammatory disease that can be prevented and/or treated according to the present invention is e.g. rheumatoid arthritis.

In a second aspect, the present invention relates to a method for inhibiting the secretion of fibroblast growth factor 2 (FGF2) by a cell, comprising the step of treating or incubating said cell in the presence of a compound according to the present invention.

In this context, the method of the present invention can be performed in vivo or in vitro. In preferred embodiments, said method is performed in vitro, i.e., it is not performed on the human or animal body.

In preferred embodiments, the cell is a tumor cell.

Suitable methods for treating or incubating a cell in the presence of a compound according to the present invention are not particularly limited and are known in the art.

The present invention is based on the biochemical characterization of the direct interaction between FGF2 and Tec kinase as well as the identification of small molecules that inhibit (i) the interaction of FGF2 with Tec, (ii) tyrosine phosphorylation of FGF2 mediated by Tec and (iii) unconventional secretion of FGF2 from cells. The specificity of these inhibitors for FGF2 is demonstrated, as tyrosine phosphorylation of a different substrate of Tec is unaffected in their presence. Building on previous evidence using RNA interference, the identified compounds corroborate the role of Tec kinase in unconventional secretion of FGF2. In addition, they are valuable lead compounds with great potential for drug development aiming at the inhibition of FGF2 dependent support of tumor growth and metastasis.

More specifically, the present invention aimed at the identification of small molecules that block the function of Tec kinase in the unconventional secretory pathway of FGF2. Following the determination of affinity between FGF2 and Tec kinase, an Alpha® protein-protein interaction assay was used to screen a library of 79,000 compounds to identify small molecules inhibitors that block binding of FGF2 to Tec kinase. Here the structure of three active, structurally related compounds has been identified that (i) block the interaction of FGF2 with Tec kinase, (ii) prevent phosphorylation of FGF2 by Tec kinase and (iii) inhibit unconventional secretion of FGF2 from cells. Based upon two inactive derivatives of these inhibitors, a highly specific mode of action of the active compounds was established. All three active compounds were found to efficiently inhibit binding of FGF2 to Tec kinase with IC50 values in the low µM range. By contrast, pleiotropic effects on general cell viability were not observed. In terms of the mechanism of inhibition, the active compounds appear to block Tec kinase auto-activation in the absence of a bound substrate. Since FGF2 cannot bind to Tec in the presence of the active compounds, tyrosine phosphorylation of FGF2 is prevented. By contrast, tyrosine phosphorylation of another substrate of Tec kinase, STAP1, remained unaffected in the presence of the active compounds. These experiments establish a high degree of specificity of the reported compounds selectively blocking FGF2 as a substrate of Tec kinase. The compounds of the present invention are the first inhibitors that are not directed at FGF2 signal transduction, but limit the amount of FGF2 secreted by tumor cells. This establishes the potential of the reported small molecule inhibitors as lead compounds for drug development, in particular with regard to tumor-induced angiogenesis and the role of FGF2 as a tumor cell survival factor.

The figure show:

FIG. 1:

The catalytic SH1 domain of Tec kinase directly interacts with FGF2 as analyzed by biochemical pull-down experiments (A) Schematic depiction of the domain structure of Tec constructs used in this study.

(B) Pull-down experiments using recombinant FGF2 covalently coupled to epoxy beads as analyzed by SDS-PAGE and Coomassie protein staining. FGF2-conjugated epoxy beads were incubated in a 1:1 molar ratio with each of the four Tec kinase derived constructs, GST-PH-TH (47.2 kDa; lane 2 and 3), GST-SH3-SH2 (47.9 kDa; lane 4 and 5), SH1 (32.9 kDa, lane 6 and 7), GST-NΔ173 Tec (80.2 kDa, lane 8 and 9). Since all constructs were used as GST fusion proteins (with the exception of the SH1 kinase domain), binding of GST alone (26.5 kDa: lanes 10 and 11) to FGF2-conjugated epoxy beads was taken along as a negative control. For each construct, bound (100%) and unbound (1%) fractions were loaded. Lane 1 contains molecular weight markers (M; PageRuler Prestained Protein Ladder: 140, 115, 80, 65, 50, 40, 30, 25, 15, 10 kDa). The shown gel is representative of 5 independent experiments.

(C) Quantification of FGF2 binding to the various Tec constructs depicted in panels A. Coomassie stained SDS gels were analyzed using the LI-COR Biosciences Odyssey infrared imaging system. The intensity of each band was quantified using Image Studio software (version 2.1.10). For each construct, binding efficiency was calculated relative to unbound material. A comparison of all constructs was conducted defining FGF2 binding efficiency towards GST-NΔ173 Tec as 100%. The statistical analysis was based upon five independent experiments. Standard deviations (SD) are shown.

FIG. 2:

Determination of the dissociation constant of the interaction between FGF2 and various forms of Tec kinase based upon fluorescence polarization (A) Fluorescence polarization experiments were conducted using fluorescein-labeled FGF2. FGF2 (at a constant concentration of 50 nM) was incubated with increasing concentrations (0 to 20 µM) of the various Tec constructs indicated. Following incubation for 3 hours at room temperature, changes in polarization (ΔPolarization in mP) were recorded. A non-linear regression analysis was conducted (GST-NΔ173 Tec: black circles, n=8; SH1 kinase domain: green squares, n=5; GST-PH-TH: blue triangles, n=3; GST-SH3-SH2: red triangles, n=3; GST: orange rhombuses, n=5) and standard errors of the mean (SEM) were calculated. As detailed in Experimental Procedures, assuming a binding stoichiometry of 1:1, dissociation constants were calculated to be 1.434 µM±0.55 (SEM) for GST-NΔ173 Tec and 1.032 µM±0.29 (SEM) for the SH1 kinase domain of Tec. FIG. 2A discloses "His6" as SEQ ID NO: 2.

(B) Competition experiments for the interaction between GST-NM 73 Tec and fluorescein-labeled FGF2. Experiments were conducted as described below. Conditions in the absence and presence of unlabeled FGF2 (50 µM) were compared. All data points were normalized based on measurements on fluorescein-labeled FGF2 alone. Errors are given as standard error of the mean (SEM). An unpaired and one-tailed t-test was conducted to assess statistical significance (* $p<0.05$,  $p<0.01$, * $p<0.001$, **** $p<0.0001$).

(C) Competition experiments for the interaction between the SH1 kinase domain of Tec and fluorescein-labeled FGF2. Experiments were conducted as described below. Conditions in the absence and presence of unlabeled FGF2 (50 µM) were compared. All data points were normalized based on measurements on fluorescein-labeled FGF2 alone. Errors are given as standard error of the mean (SEM). An unpaired and one-tailed t-test was conducted to assess statistical significance (* $p<0.05$,  $p<0.01$, * $p<0.001$, **** $p<0.0001$).

FIG. 3:

A protein-protein interaction assay designed to screen small molecule libraries for compounds inhibiting FGF2 binding to Tec kinase The direct interaction between FGF2 and Tec kinase was quantified using Alpha® technology (red spheres). A His-tagged form of FGF2 and GST-NM 73Tec were used along with glutathione-coated donor and Ni-NTA-coated acceptor beads as explained in Experimental Procedures. As a control, an unrelated protein pair, His-tagged MBP-CARP and GST-Titin (black spheres), were used. Alpha® signals were measured in the presence of increasing concentrations of NΔ25FGF2, a competitor for binding of His-tagged FGF2 to GST-NΔ173 Tec. Alpha® signals are expressed as percentage of the median of the maximal Alpha® signal (tagged proteins in the absence of the NΔ25FGF2 competitor) that was set to 100% in each independent experiment. Data points represent the mean of 8 independent experiments, each of with consisting of 3 technical replicates. Experimental deviations are expressed as standard error of the mean (SEM). Data were fitted with a non-linear regression model. The $K_D$ of the GST-NΔ173 Tec/N26ΔFGF2 complex was calculated to be 0.63 μM±0.033 μM (SEM; $r^2=0.9986$).

FIG. 4:

Chemical structures of active (#6, #14 and #21) versus inactive (#18 and #19) compounds EMBL IDs are provided as a reference to the internal database of the Chemical Biology Core Facility at EMBL Heidelberg.

Figure 3:
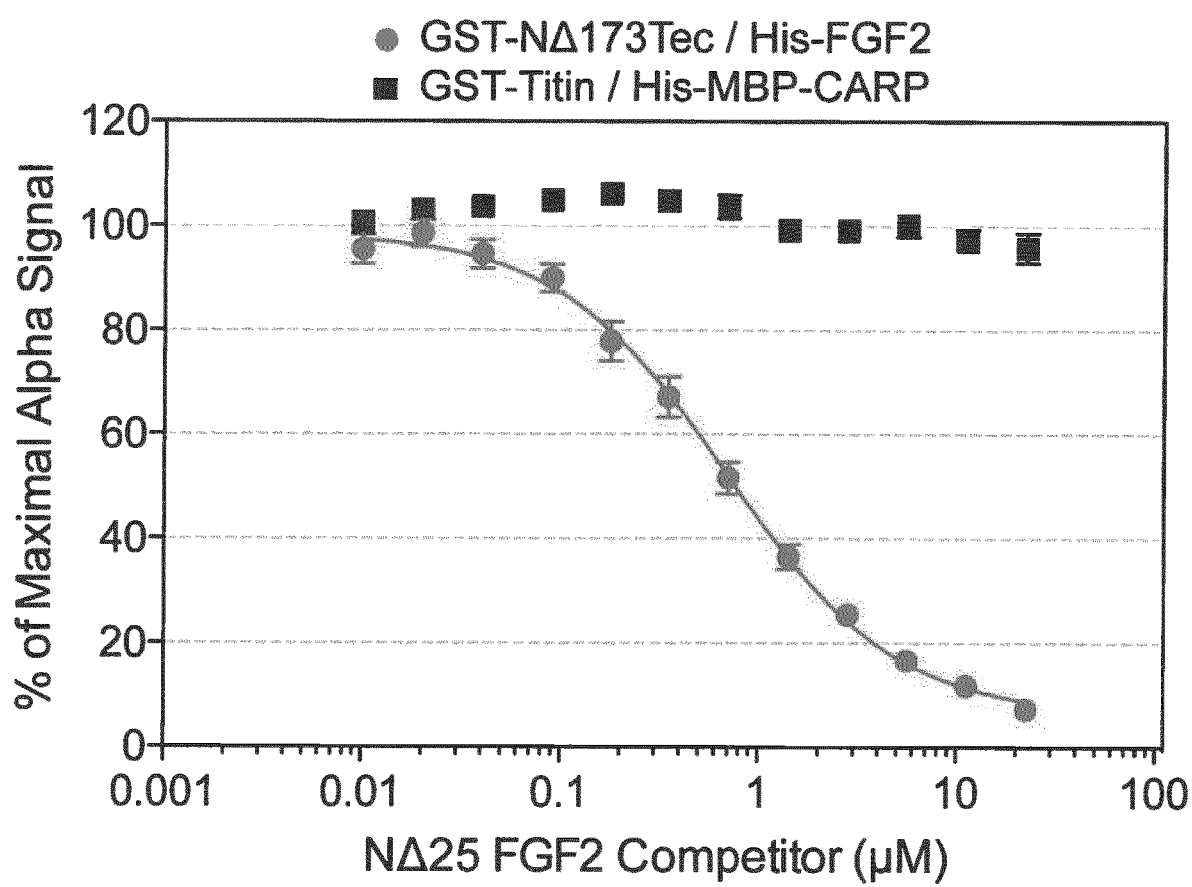

FIG. 5:

Determination of dose-response curves for active (#6, #14 and #21) versus inactive (#18 and #19) compounds Alpha® protein-protein interaction assays with His-tagged FGF2 (125 nM) and GST-NΔ173 Tec (31.25 nM) (blue spheres) as well as His-tagged MBP-CARP (20 nM) and GST-titin (20 nM) (red squares) were conducted as described in the legend of FIG. 3 and in Experimental Procedures. Additionally, as a technical control, a single fusion protein containing both a GST- and a His-tag was used (20 nM; black triangles). Dose response curves were recorded with the three active compounds (#6, #14 and #21) as well as the two control compounds (#18 and #19) (FIG. 4). For each compound four independent experiments (each of which was conducted in three technical replicates) were performed. Data points were fitted using the non-linear regression function log (inhibitor) vs. response—variable slope (four parameters). Data were evaluated using GraphPad Prism (v5 for Mac OS X). Standard deviations are shown.

(A) Dose-response curves of compound #6.
IC50 (His-FGF2/GST-NΔ173 Tec)=8.9 μM±1.1 (SEM)
(B) Dose-response curves of compound #14.
IC50 (His-FGF2/GST-NΔ173 Tec)=7.0 μM±1.1 (SEM)
(C) Dose-response curves of compound #21.
IC50 (His-FGF2/GST-NΔ173 Tec)=11.7 μM±1.0 (SEM)
(D) Dose-response curves of compound #18.
(E) Dose-response curves of compound #19.

FIG. 6:

Small molecule inhibition of Tec kinase mediated tyrosine phosphorylation of FGF2

FGF2 tyrosine phosphorylation and Tec kinase auto-phosphorylation were reconstituted with purified components based on a Western analysis using anti-phosphotyrosine antibodies directed against an FGF2-derived phosphopeptide. In vitro phosphorylation experiments were conducted in the absence (1% DMSO mock control) and presence of the small molecule inhibitors (#6, #14, #21; 50 μM in 1% DMSO) and control compounds (#18, #19; 50 μM in 1% DMSO) introduced in FIGS. 4 and 5. Fluorescent secondary antibodies were used to detect antigens employing the LI-COR Odyssey imaging platform. M=PageRuler Prestained Protein Ladder. For details, see Experimental Procedures.

(A) Representative Western analysis using antibodies recognizing both phosphorylated FGF2 [FGF2 (P)] and Tec kinase in its auto-phosphorylated form [GST-NΔ173 Tec (P)]. Lane 1 contains molecular weight markers of 140, 115, 80, 65, 50, 40, 30, 25, 15 and 10 kDa.

(B) Coomassie-stained SDS gel corresponding to the Western analysis shown in panel A. Lane 1 contains molecular weight markers of 140, 115, 80, 65, 50, 40, 30, 25, 15 and 10 kDa.

(C) Quantification and statistical analysis of 5 independent experiments using the LI-COR Odyssey imaging platform. Following background normalization, the average of FGF2 tyrosine phosphorylation under mock conditions was defined as 100% activity. Standard deviations are shown. A one-tailed and unpaired T-test was conducted to test significance (* $p<0.05$,  $p<0.01$, * $p<0.001$, **** $p<0.0001$). "NS" indicates absence of significant differences.

FIG. 7:

Selectivity of small molecule inhibitors towards Tec kinase mediated tyrosine phosphorylation of FGF2

FGF2 and STAP1 tyrosine phosphorylation as well as Tec kinase auto-phosphorylation were analyzed as described in the legend to FIG. 6 and in Experimental Procedures. In vitro phosphorylation experiments were conducted in the absence (1% DMSO mock control) and presence of the small molecule inhibitors (#6, #14, #21; 50 μM in 1% DMSO) and control compounds (#18, #19; 50 μM in 1% DMSO) introduced in FIGS. 4 and 5. A Western analysis was conducted using anti-phosphotyrosine antibodies (anti-pY-FGF2 for FGF2 and Tec as well as anti-pY-4G10 for STAP1). M=PageRuler Prestained Protein Ladder: 140, 115, 80, 65, 50, 40, 30, 25, 15, 10 kDa. Fluorescent secondary antibodies were used to detect and quantify antigens using the LI-COR Odyssey imaging platform. In panels D, E and F, following normalization based upon background signals detected in the absence of Tec kinase or ATP, the average of the signals detected under mock conditions was defined as 100% activity. Standard deviations are shown. A one-tailed and unpaired T-test was conducted to assess statistical significance (* $p<0.05$,  $p<0.01$, * $p<0.001$, **** $p<0.0001$). "NS" indicates absence of significant differences.

(A) Tec kinase mediated tyrosine phosphorylation of FGF2 in the absence and presence of active and inactive compounds (50 μM each)

(B) Tec auto-phosphorylation in the absence of a substrate measured in the absence and presence of active and inactive compounds (50 μM each)

(C) Tec kinase mediated tyrosine phosphorylation of STAP1 in the absence and presence of active and inactive compounds (50 μM each). Following protein transfer to PDVF, membranes were cut to stain the upper part with anti-pY-FGF2 antibodies (to detect Tec auto-phosphorylation) and the lower part with anti-pY-4G10 antibodies (do detect phosphorylated STAP1)

(D) Quantification of the Western analysis shown in panel A (E) Quantification of the Western analysis shown in panel B (F) Quantification of the Western analysis shown in panel C

FIG. 8:

Small molecule inhibitors blocking Tec kinase mediated tyrosine phosphorylation of FGF2 inhibit unconventional secretion of FGF2 from cells A stable CHO cell line expressing an FGF2-GFP fusion protein in a doxycycline-dependent manner was used to quantify FGF2 transport to cell surfaces in the absence and presence of the small molecule inhibitors introduced in FIGS. 4, 5, 6 and 7. As detailed in Experimental Procedures, following cultivation of cells in the presence of compounds as indicated and induction of FGF2-GFP expression, proteins localized to the cell surface were biotinylated with a membrane-impermeable reagent. Following quenching of the biotinylation reagent, biotinylated proteins were purified using streptavidin beads. Following SDS-PAGE analyzing both the total lysate (input termed "cells"; 1.7%) and the biotinylated cell surface fraction (33%), a Western analysis was conducted to detect the secreted population of FGF2-GFP. Using appropriate fluorescent secondary antibodies, both FGF2-GFP and GAPDH (used as a control protein restricted to the intracellular space) were quantified using the LI-COR Odyssey imaging platform. FGF2-GFP secretion quantified under mock conditions (0.5% DMSO) was defined as 100% secretion efficiency. Standard deviations are shown from three independent experiments, each of which was conducted in two technical replicates. A two-tailed and unpaired T-test was conducted to assess statistical significance (* $p<0.05$,  $p<0.01$, * $p<0.001$, **** $p<0.0001$). "NS" indicates absence of significant differences.

(A) Quantification of FGF2-GFP secretion from cells in the absence and presence of compound #6 (active)

(B) Quantification of FGF2-GFP secretion from cells in the absence and presence of compound #14 (active)

(C) Quantification of FGF2-GFP secretion from cells in the absence and presence of compound #21 (active)

(D) Quantification of FGF2-GFP secretion from cells in the absence and presence of compound #18 (inactive)

(E) Quantification of FGF2-GFP secretion from cells in the absence and presence of compound #19 (inactive)

FIG. 9:

Small molecule inhibitors blocking Tec kinase mediated tyrosine phosphorylation of FGF2 do not exert apparent pleiotropic effects on cell viability and proliferation CHO cells expressing mCherry fused to a nuclear localization signal (NLS) were used to monitor potential pleiotropic effects on cell viability and proliferation of the compounds introduced in FIG. 4. Cell proliferation was monitored by absolute counting of fluorescent nuclei using an IncuCyte Zoom live cell imaging microscope (Essen Biosciences). As a starting density, $1 \times 10^4$ cells were cultivated per experimental condition in 96-well plates. The actual cell numbers measured at t=0 was set to 100%. Cell proliferation was monitored at 37° C. for 72 hours under mock conditions (0.5% DMSO) as well as in the presence of 10, 25 and 50 µM of each compound as indicated. Cell numbers were determined in intervals of two hours. The experiments shown are representative for a total of 4 biological replicates, each of which contained three technical replicates for every single data point. Standard deviations are shown.

The present invention will be further illustrated in the following examples without being limited thereto.

EXAMPLES

Experimental Procedures

Expression and Purification of Recombinant Proteins

Several recombinant forms of both FGF2 and Tec kinase were used in this study. This includes authentic FGF2 (154 amino acids; 18 kDa form), His-tagged FGF2 and NΔ25FGF2 (129 amino acids) as well as four forms of Tec kinase with the domain structures depicted in FIG. 1A (GST-NΔ173 Tec, GST-PH-TH, GST-SH3-SH2 and the SH1 kinase domain).

All forms of FGF2 were expressed and purified from *E. coli* according to standard procedures. Untagged FGF2 was expressed as an N-terminal GST fusion protein. Following binding to glutathione affinity beads (Glutathione Sepharose™ 4 Fast Flow, GE Healthcare), the GST tag was cleaved off by thrombin treatment. The product was collected and loaded onto a heparin affinity column (HiTrap Heparin HP, GE Healthcare) and, following elution under high salt conditions, a homogenous fraction of untagged FGF2 was collected. His-tagged FGF2 was purified by Ni-NTA affinity (HisTrap FF, GE Healthcare) and heparin affinity chromatography. N-terminally truncated FGF2 (NΔ125FGF2; 129 amino acids) lacking the first 25 amino acids was expressed and purified to homogeneity using heparin affinity chromatography. Purified His-STAP1 was purchased from Hölzel Diagnostika (Cat. # GWB-P0486E-100).

All Tec kinase-derived constructs depicted in FIG. 1A (GST-NΔ173 Tec, GST-PH-TH, GST-SH3-SH2 and the SH1 kinase domain) were expressed in SF9 insect cells using the Baculovirus expression system. GST-NΔ173 Tec, GST-PH-TH and GST-SH3-SH2 were purified by glutathione affinity chromatography (GSTrap™ FF, GE Healthcare). By contrast, the SH1 kinase domain was purified based on an N-terminal His-tag employing Ni-NTA affinity chromatography. The His-tag was removed proteolytically followed by a second purification step based on size exclusion chromatography (HiLoad 16/600 Superdex™ 200 pg, GE Healthcare) yielding a homogenous preparation of the SH1 kinase domain.

Pull Down Experiments Using FGF2 Conjugated Epoxy Beads and Various Forms of Tec Kinase (FIG. 1)

Untagged FGF2 (2 mg) was covalently conjugated to epoxy-activated Sepharose™ beads 6B (600 mg; #17-0480-01, GE Healthcare) based on the manufacturer's instructions. FGF2-conjugated beads (2.5 µl bed volume containing 1.5 µM FGF2) was incubated on a rotating platform for 2 hours at room temperature with each of the Tec variant forms depicted in FIG. 1A (final concentration=1.5 µM in a total volume of 200 µl). The binding buffer contained 50 mM Tris-HCl (pH 7.4), 150 mM NaCl, 1 mM benzamidine, 0.05% Tween 20, 1 mM DTT. Proteins bound to beads were collected by centrifugation (7000 rpm, 4° C., 5 minutes). The beads were washed extensively with binding buffer. Bound proteins were eluted with SDS sample buffer and, following boiling at 95° C., bound (100%) and unbound (1%) fractions were analyzed by SDS-PAGE (NuPAGE 4-12% Bis-Tris pre-casted gels from Novex). Protein gels were stained with Coomassie InstantBlue (Expedeon). Marker proteins of 140, 115, 80, 65, 50, 40, 30, 25, 15, 10 kDa (PageRuler Prestained Protein Ladder; #26616, Thermo Scientific) were used to monitor migration behavior of proteins.

Determining the Dissociation Constant for the Interaction Between Tec Kinase and FGF2 Employing Steady-State Fluorescence Polarization (FIG. 2)

To determine binding affinity between Tec kinase and FGF2, steady-state fluorescence polarization was used. His-tagged FGF2 was labeled with fluorescein-5-maleimide (F150, Thermo Fisher Scientific) covalently modifying a cysteine residue on the molecular surface of FGF2. Briefly, 100 nmol of His-tagged FGF2 (dissolved in 50 mM Tris-HCl, 150 mM NaCl, pH 7.4) were incubated with a 10-fold molar excess of Tris (2-carboxyethyl) phosphine hydrochloride (TCEP; Pierce) at room temperature. Fluorescein-5-maleimide (44 nmol) was added resulting in a final volume of 0.8 ml. Following incubation for 20 minutes at room temperature, residual amounts of free dye were removed using PD-10 desalting columns (GE Healthcare). The labeled protein was concentrated using a Vivaspin 500 system with a cut-off of 10 kDa (Sartorius). Based on the extinction coefficients of both His-tagged FGF2 and fluroscein-5-maleimide, the degree of labeling was determined to be 30%. The final preparation of fluorescein-labeled FGF2 had a protein concentration of 1.7 mg/ml. All proteins used in these assays were adjusted to the same buffer (50 mM Tris-HCl, 150 mM NaCl, pH 7.4) using PD-10 desalting columns (GE Healthcare). Absolute protein concentrations were determined based upon the extinction coefficients calculated for each protein and measuring absorption at 280 nm using a NanoDrop 1000 spectrophotometer.

In order to determine the dissociation constants for the interaction of FGF2 with various forms of Tec kinase, fluorescein-labeled FGF2 (50 nM) was incubated with increasing concentrations (0 to 20 µM as indicated) of GST-NΔ173 Tec, GST-PH-TH, GST-SH3-SH2 and the SH1 kinase domain of Tec (FIG. 2A). In addition, GST alone was taken along as negative control. Following incubation for 3 hours at room temperature in binding buffer (50 mM Tris-HCl, 150 mM NaCl, pH 7.4, 0.1% BSA, 0.05% Tween 20; final volume=10 µl), fluorescence polarization experiments were conducted by excitation of labeled FGF2 with polarized light. The interaction between fluorescein-labeled FGF2 and unlabeled forms of Tec kinase was measured as the progressive increase of fluorescence polarization (ΔPolarization) as a function of the protein concentration of the various forms of Tec kinase. Data were collected with a SpectraMax M5 plate reader from Molecular Devices equipped with SoftMax Pro software (v5.4.5 for Mac OS X). Data were expressed as change in polarization (ΔPolarization) normalizing each individual replicate by the corresponding polarization value of fluorescein-labeled FGF2 in the absence of Tec kinase. The corresponding binding curve was used to calculate the dissociation constant with data fitting using the following quadratic equation:

$$Y=Fo+(Fm-Fo)*[(x+L+K)/2-\text{sqrt}((x+L+K)^2/4-x*L)]/L$$

Fo and Fm represent the bottom and the top of the binding curve, x is the binding partner concentration, L is the concentration of the labeled protein and K is the dissociation constant. Fitting was performed using GraphPad Prism (v5.0 for Mac OS X).

To establish a specific interaction between FGF2 and GST-NΔ173 Tec as well as the SH1 kinase domain of Tec, competition experiments with unlabeled FGF2 were performed (FIGS. 2B and 2C). Experiments were conducted at 50 nM fluorescein-labeled His-FGF2 in the presence and absence of 1.25 µM of GST-NΔ173 Tec or the SH1 kinase domain under the conditions described above. In addition, conditions were varied based upon the presence or absence of an unlabeled FGF2 competitor molecule at 50 µM.

A Protein-Protein Interaction Assay Designed to Screen Small Molecule Libraries for Compounds Inhibiting FGF2 Binding to Tec Kinase (Alphascreen® Assay)

To quantify the interaction of FGF2 with Tec kinase under screening conditions, an assay was established based upon Alpha® technology. Briefly, this methodology is based on a pair of proteins of interest that bind to Alpha® donor and acceptor beads, respectively. Upon excitation of donor beads at 680 nm, singlet oxygen species are produced that can diffuse within a range of 200 nm. If donor and acceptor beads are in close proximity due to the protein-protein interaction, singlet oxygen species will transfer energy to acceptor beads. This in turn causes emission of light with a wave length of 520 nm that is detected as the Alpha® signal.

The optimal concentrations of His-tagged FGF2 and GST-tagged NΔ173 Tec in the Alphascreen were determinate in a cross-titration experiment (not shown) to be 31.25 nM and 62.5 nM, respectively. To determine binding affinity between His-tagged FGF2 and GST-NM 73 Tec and to assess the specificity of the Alpha signal for the Tec-FGF2 interaction, competition experiments were conducted with an untagged version of FGF2 (NΔ25-FGF2) (FIG. 3). As specificity control for the competition by untagged FGF2 an Alpha® assay was conducted using an unrelated protein-protein pair (GST-Titin/His-MBP-CARP at a final concentration of 20 nM each). Briefly, after incubation of the proteins for 75 min at room temperature in PBS (supplemented with 0.1% BSA, 0.05% Tween 20), glutathione donor beads (#6765300, PerkinElmer) and Ni-NTA acceptor beads (#6760619, PerkinElmer) were added at a concentration of 7.5 µg/ml in a final volume of 15 µl followed by a second incubation for additional 2 hours. All Alpha® assays were carried out in white low volume 384-well plates (#6008280, ProxiPlate™) and read in an EnVision plate reader (Perkin Elmer). The obtained data points were fitted with GraphPad Prism (v5.00 for Mac OS X) using a cubic equation to calculate the dissociation constant for the GST-NΔ173Tec/FGF2 complex.

Screening of Small Molecule Collection for Inhibitors of the FGF2-Tec Interaction AlphaScreen experiments were performed as described above. GST-NΔ173 Tec and His-tagged FGF2 were combined in screening buffer (20 mM Tris-HCl, 150 mM NaCl, 1 mM DTT, 0.1% BSA, 0.05% Tween 20) and pre-incubated for 60 min in the presence of compounds or the solvent DMSO. Afterwards, glutathione-coated donor and Ni-NTA-coated acceptor beads were added. Following 60 min of incubation, Alpha® signals were recorded using an EnVision™ plate reader (PerkinElmer). In the primary screen, 79,000 compounds were tested at a final concentration of 40 µM. This scaffold-based collection was assembled from the vendors AMRI, Enamine and Chembridge. Reordered or synthesized compounds were tested in dose-response using an eleven-fold 1:2 serial dilution starting at 200 µM. The serially diluted compounds were also tested in a deselection assay with a non-related protein pair, GST-Titin and His-tagged MBP-CARP (20 nM each), to evaluate the specificity of compounds inhibiting the interaction of GST-NM 73 Tec and FGF2. Finally GST-His-Biotin, a fusion protein containing both, a N-terminal GST- and a C-terminal His-tag, was used at 20 nM as an additional technical control. To generate dose-response curves and corresponding IC50 values (FIG. 5), compounds were reordered from Enamine (Compound #6: # Z51196782; compound #14: # Z15516480; compound #21: # Z17100166; compound #18: # BJ01-04; compound #19: # BJ01-05). Compound powders were dissolved in DMSO with a stock concentration of 10 mM, incubated for 10 min at 37° C. and further treated by sonication for 5 min at room temperature. Compound stock solutions were stored at −20° C.

Biochemical Reconstitution of Tec Kinase Mediated Tyrosine Phosphorylation of FGF2 and STAP1 (FIGS. 6 and 7)

A Tec kinase in vitro phosphorylation assay was established to test the inhibitory potential and selectivity of the small molecule inhibitors reported in this study (FIGS. 6 and 7). Tyrosine phosphorylation of FGF2 and STAP1, another established substrate of Tec kinase, was tested in a final volume of 100 µl (60 mM Hepes pH 7.5, 3 mM $MgCl_2$, 20 µM ATP, 3 µM Sodium orthovanadate, 1.2 mM DTT, 50 ng/µl PEG 20000, 0.05% w/v Tween 20, 0.001% BSA). GST-NΔ173Tec (60 nM) was incubated in the absence (1% DMSO mock control) or presence of each compound (50 µM in 1% DMSO). Where indicated, reactions contained 250 nM of either FGF2 or 250 nM STAP1 (Hölzel Diagnostika, # GWB-P0486E-100). Following incubation at 30° C. for 45 minutes (corresponding to the midpoint of linear product formation), the reaction was terminated using SDS sample buffer and boiling for 4 minutes at 95° C. Proteins were separated by SDS-PAGE (4-12% Bis-Tris gradient) and transferred to PVDF membranes. Phosphorylation levels of GST-NΔ173 Tec (auto-phosphorylation), FGF2 and STAP1 were quantified by a Western analysis using polyclonal anti-phosphotyrosine antibodies raised against a FGF2-derived synthetic peptide containing a phosphorylated tyrosine residue (ANRpYLAMKED; SEQ ID NO: 1). This antibody was found to recognize both tyrosine-phosphorylated FGF2 and auto-phosphorylated Tec kinase. Phosphorylation levels of STAP1 were monitored using a monoclonal anti-phosphotyrosine antibody (clone 4G10®, #05-321, Merck Millipore). Appropriate fluorescent secondary antibodies (goat anti-rabbit IgG conjugated with Alexa Fluor® 680, # A-21076, Life Technologies; goat anti-mouse IgG conjugated with Alexa Fluor® 680, # A-21057, Life Technologies) were used to quantify all antigens employing the LI-COR Odyssey infrared imaging platform. In FIG. 6B, an SDS gel corresponding to the Western analysis shown in FIG. 6A was stained with Coomassie InstantBlue (Expedeon) to control for protein amounts and purity. The PageRuler Prestained Protein Ladder from was used containing marker proteins with the following molecular weights: 140, 115, 80, 65, 50, 40, 30, 25, 15, 10 kDa (Thermo Scientific/Fermentas, #26616).

Quantification of FGF2 Secretion Using Cell Surface Biotinylation (FIG. 8)

Secreted FGF2 remains bound to heparan sulfates on cell surfaces without release into cell culture supernatants. This allows for biochemical detection of the secreted population based upon cell surface biotinylation experiments. CHO cells stably expressing FGF2-GFP in a doxycycline-dependent manner were cultivated in the presence of compounds #6, #14, #21, #18 and #19 (see FIGS. 4 and 5) at 10 µM, 25 µM and 50 µM in 0.5% DMSO (final concentration) as well as under mock conditions. Following incubation at 37° C. for 24 hours, in the continued presence of compounds, doxycycline was added to induce expression of FGF2-GFP. After another 16 hours of cultivation at 37° C., cells were treated with a membrane-impermeable biotinylation reagent, EZ-Link Sulfo-NHS-SS-Biotin (sulfosuccinimidyl-2-[biotinamido]ethyl-1,3-dithiopropionate, #21331; Pierce), targeting primary amines on cell surface proteins. Following quenching and detergent-mediated cell lysis, biotinylated and non-biotinylated material was separated from each other using streptavidin beads (UltraLink immobilized streptavidin, Pierce). Aliquots from the total cell lysate (corresponding to input) and aliquots of the purified biotinylated fractions (corresponding to the secreted population) were subjected to SDS-PAGE and a Western analysis. Affinity-purified anti-GFP antibodies and monoclonal anti-GAPDH antibodies (Lifetech-Ambion) were used to detect FGF2-GFP and GAPDH, respectively. GAPDH was used as a control protein localized exclusively to the intracellular space. Using appropriate fluorescent secondary antibodies, FGF2-GFP and GAPDH were quantified using the LI-COR Odyssey imaging platform. FGF2 secretion under mock conditions (0.5% DMSO) was defined as 100% secretion efficiency.

Quantitative Analysis of Cell Proliferation (FIG. 9)

To detect potential pleiotropic effects on cell viability of small molecule inhibitors, cell proliferation was monitored in the absence and presence of the compounds introduced in FIG. 4. CHO cells constitutively expressing mCherry fused to a nuclear localization signal (NLS) were cultivated under conditions equivalent to the experiments shown in FIG. 8. Cell proliferation was quantified in real time employing an IncuCyte® Zoom live cell imaging microscope (Essen BioScience), providing an absolute quantification of fluorescent cell nuclei with kinetic resolution (29). In this way, cell proliferation was monitored for 72 hours (with measurements conducted every 2 hours) under the conditions indicated (FIG. 9).

Example 1

Biochemical Characterization of FGF2 Binding to Tec Kinase

A first set of experiments was based on biochemical pull-down experiments to probe for a direct interaction between FGF2 and Tec kinase. FGF2 was expressed in *E. coli*, purified to homogeneity and covalently coupled to epoxy beads. Various constructs of Tec kinase were expressed and purified from insect cells (FIG. 1A). These experiments revealed that the kinase domain (SH1) of Tec is sufficient for binding to FGF2 (FIG. 1B). Consistently, a construct containing the SH1, SH2 and SH3 domains of Tec (GST-NΔ173 Tec) did bind to FGF2 as well (FIG. 1B). By contrast, constructs restricted to either the pleckstrin homology (PH) and Tec homology (TH) domains (GST-PH-TH), the SH3/SH2 domains (GST-SH3-SH2) or GST alone did not bind to FGF2 (FIG. 1B). The Coomassie stained gel shown in FIG. 1B was quantified using the LI-COR imaging system (FIG. 1C).

To determine affinity between FGF2 and Tec kinase, steady-state fluorescence polarization experiments were conducted. FGF2 was fluorescently labeled as explained in 'Experimental Procedures' and binding experiments with various Tec constructs were performed in solution (FIG. 2A). Similar to the results shown in FIG. 1, a direct interaction of FGF2 with both the SH1 kinase domain of Tec and GST-NΔ173 Tec was observed. The significance of these findings was confirmed by competition experiments using unlabeled FGF2. In the presence of 50 µM unlabeled FGF2, the interaction of labeled FGF2 with both the kinase domain (SH1) of Tec (FIG. 2B) and GST-NΔ173 Tec (FIG. 2C) was blocked. By contrast, FGF2 did not bind to GST-PH-TH, GST-SH3-SH2 or GST alone (FIG. 2A). To determine affinity between FGF2 and Tec kinase, fluorescently labeled FGF2 (50 nM) was incubated with increasing concentrations (0.078 to 20 µM) of the various Tec constructs indicated (FIG. 2A). Data points were fitted and dissociation constants were calculated as explained in 'Experimental Procedures'. Dissociation constants of 1.434 µM±0.55 (SEM) and 1.032 µM±0.29 (SEM) were obtained for GST-NΔ173 Tec and the kinase domain (SH1) of Tec, respectively.

Example 2

Large-Scale Small Molecule Screening for Inhibitors that Block Binding of FGF2 to Tec Kinase To identify small molecule inhibitors that prevent the interaction between FGF2 and Tec kinase, a screening assay was established based upon Alpha® technology. His-tagged FGF2 and GST-tagged NΔ173 Tec were coupled to Alpha® donor and acceptor beads, respectively. Using a cross titration experiment, suitable protein concentrations of 31.25 nM (FGF2) and 62.5 nM (NΔ173 Tec) were identified providing a satisfying signal to noise ratio. Under these conditions, affinity between FGF2 and NΔ173 Tec was analyzed using competition experiments. Based upon a titration curve with an untagged variant form of FGF2, NΔ25FGF2, a dissociation constant of 0.63 µM±0.03 µM (SEM) was determined (FIG. 3). When analyzing an unrelated pair of interacting proteins, GST-Titin and His-tagged MBP-CARP, NΔ25FGF2 did not affect the Alpha® signal (FIG. 3). These findings establish a specific and direct interaction between FGF2 and NΔ173 Tec with a dissociation constant comparable to the results obtained in steady-state fluorescence polarization experiments (FIG. 2).

To identify small molecule inhibitors of the interaction between FGF2 and NΔ173 Tec, a small molecule compound library was screened using the Alpha® protein-protein interaction assay described in FIG. 3. This scaffold-based collection comprises 79,000 compounds. The screening assay was performed at a final compound concentration of 40 μM and revealed 661 compounds that inhibit the interaction between FGF2 and NΔ173 Tec by more than 40%. The Titin/CARP assay described in FIG. 3 was used to deselect unspecific compounds. In addition, compounds that were found active in previous screening campaigns based on Alpha® technology were deselected. This procedure resulted in a preliminary hit list of 141 potential compounds inhibiting the interaction between FGF2 and NΔ173 Tec. These compounds were reordered and tested in dose-response experiments to determine IC50 values. A set of 28 compounds was found to be characterized by IC50 values of less than 100 μM. Based upon (i) inhibitory strength in the primary screening assay, (ii) lack of activity in the Titin/CARP deselection assay and (iii) inhibitory potency in in vitro phosphorylation experiments (see FIGS. 6 and 7), a final set of three highly active compounds (#6, #14 and #21) was identified (FIG. 4). In addition, two structurally related but inactive compounds (#18 and #19) were selected as controls for all subsequent experiments. With regard to chemical identities, compounds #6, #14 and #19 are based on a 4H-Pyrido[1,2-a]pyrimidinone scaffold. Compounds #6 and #14 have a 2-hydroxymethyl substituent that is condensed to a substituted pyrrole carboxylic acid moiety via an ester function. This ester linkage is potentially metabolically labile in vivo due to cleavage by esterases. In addition, compound #6 contains a methyl ester on the pyrrole moiety that is likely to be cleaved in vivo. Compound #19 is a more stable analogue of compound #14 that replaces the ester linkage with a much more metabolically stable amide moiety. However this appears to abolish all activity, although the absence of the bromo substituent in compound #19 makes a definitive conclusion on the importance of the linker difficult. It is clear, however that the 1-(2,4-dimethyl-1H-pyrrol-3-yl)ethanone moiety alone is not sufficient for activity. Compound #21 has a 3H-imidazo[4,5-b]pyridine scaffold and contains the 1-(2,4-dimethyl-1H-pyrrol-3-yl)ethanone moiety also found in compounds #14 and #19. The imidazo-pyridine scaffold of #21 is partially isosteric to the pyrido-pyrimidone scaffold of #14, and indeed this compound retains activity. In addition, the ester linkage is replaced by a sulfanyl-acetyl type link. This indicates that the ester linkage found in #6 and #14 can be replaced with more metabolically stable alternatives. Compound #18 has a [1,2,4]triazolo[1,5-a]pyrimidine scaffold which is also partially isosteric to the pyrido-pyrimidone scaffold of #14. Instead of the pyrrole substituent present in all other compounds, it contains a coumarin moiety. The simultaneous modification of both termini of the molecule plus a different amide linker makes this compound rather different from the other active compounds and it can be considered as a negative control compound.

Example 3

Determination of Inhibitory Potential of Active Compounds

Beyond the dose-response experiments that were conducted under screening conditions (see above), the inhibitory potential of the identified compounds along with their inactive derivatives was carefully analyzed (FIG. 5). Using the Alpha® protein-protein interaction assay, IC50 values of 8.9 μM±1.1 (SEM) for compound #6 (FIG. 5A), 7.0 μM±1.1 (SEM) for compound #14 (FIG. 5B) and 11.7 μM±1.0 (SEM) for compound #21 (FIG. 5C) were determined. By contrast, the inactive compounds #18 (FIG. 5D) and #19 (FIG. 5E) did not exert significant inhibition of the interaction between His-tagged FGF2 and GST-NΔ173 Tec at concentrations of up to 200 μM. Importantly, neither the active nor the inactive compounds did affect the de-selection assay probing for a potential inhibitory activity towards the unrelated interaction between Titin and CARP (FIG. 5A-E). Also, none of the compounds affected a technical control assay in which a single fusion protein (GST-His-Biotin) was used to directly link Alpha donor and acceptor beads (FIG. 5A-E). The combined findings from FIG. 5 establish compounds #6, #14 and #21 (FIG. 4) as selective and potent inhibitors of the interaction between FGF2 and NΔ173 Tec that are characterized by IC50 values in the low μM range.

Example 4

Small Molecule Inhibition of Tec Kinase Catalyzed Tyrosine Phosphorylation of FGF2

To analyze the potential of the active compounds beyond protein-protein interaction assays (FIG. 5), it was analyzed whether they affect tyrosine phosphorylation of FGF2 mediated by Tec kinase (FIG. 6). Purified FGF2 and NΔ173 Tec were incubated under the conditions indicated. Tyrosine phosphorylation of both GST-NΔ173 Tec (auto-phosphorylation) and FGF2 was monitored by a quantitative Western analysis using antibodies directed against a phosphopeptide derived from FGF2. These antibodies also recognize the auto-phosphorylated form of GST-NΔ173 Tec (FIG. 6A). Protein amounts were monitored for all conditions employing SDS-PAGE and Coomassie staining (FIG. 6B). These experiments revealed potent inhibition of FGF2 tyrosine phosphorylation by the three active compounds #6, #14 and #21 (FIG. 6A). The Western analysis shown in FIG. 6A was quantified revealing about 75% inhibition by compound #6 and almost quantitative inhibition by compounds #14 and #21 (FIG. 6C). Interestingly, autophosphorylation of NΔ173 Tec was affected as well, albeit less efficiently compared to FGF2 phosphorylation (FIGS. 6A and 6C). By contrast, the control compounds #18 and #19 neither affected NΔ173 Tec auto-phosphorylation nor FGF2 tyrosine phosphorylation (FIGS. 6A and 6C). Therefore, beyond the analysis of protein-protein interactions (FIG. 5), these experiments establish inhibitory potency of the identified active compounds with regard to FGF2 tyrosine phosphorylation mediated by Tec kinase.

Example 5

Selectivity of Active Compounds Regarding Different Substrates of Tec Kinase

To test whether the active compounds #6, #14 and #21 selectively block Tec mediated tyrosine phosphorylation of FGF2, another established substrate of Tec, STAP1, was tested. In this independent set of experiments, the inhibitory potency of compounds #6, #14 and #21 towards Tec mediated FGF2 tyrosine phosphorylation was confirmed (FIGS. 7A and 7D). Interestingly, the observed inhibition of Tec autophosphorylation was not only observed in the presence of FGF2 but, albeit less efficiently, in its absence as well (FIGS. 7B and 7E). This effect was particularly evident for compounds #6 and #21. Finally, it was tested whether the active compounds affect Tec mediated tyrosine phosphorylation of STAP1 (FIGS. 7C and F). Intriguingly, in the presence of STAP1, neither auto-phosphorylation of NΔ173 Tec nor tyrosine phosphorylation of STAP1 was affected by any of the compounds that were found active towards FGF2 phosphorylation. These findings suggest that the active compounds #6, #14 and #21 bind to Tec kinase and prevent recruitment of FGF2 resulting in a loss of FGF2 tyrosine phosphorylation. In the absence of a bound substrate, autophosphorylation of NΔ173 Tec is inhibited as well. However, in the presence of an unrelated substrate such as STAP1, neither auto-phosphorylation of NΔ173 Tec nor tyrosine phosphorylation of STAP1 is affected by compounds #6, #14 and #21. Therefore, these combined findings establish selectivity of these inhibitors towards FGF2 as a substrate of Tec, reflecting the design of the original small molecule screening procedure aiming at FGF2/Tec protein-protein interaction inhibitors.

Example 6

Small Molecule Inhibitors Blocking FGF2 Tyrosine Phosphorylation Inhibit FGF2 Secretion from Cells Based upon the biochemical reconstitution experiments shown in FIGS. 5, 6 and 7, it was determined whether the active compounds #6, #14 and #21 affect FGF2 secretion from cells (FIG. 8). Again, the inactive compounds #18 and #19 were taken along as controls. To quantify FGF2 secretion, a well-established biotinylation assay was used to detect FGF2 bound to heparan sulfates on cell surfaces. Briefly, following doxycycline-induced expression of FGF2-GFP, proteins present on cell surfaces were modified using a membrane-impermeable biotinylation reagent. Following cell lysis, biotinylated proteins (=cell surface) were separated from non-biotinylated proteins (=intracellular) using streptavidin beads. Samples were subjected to SDS-PAGE followed by a Western analysis of FGF2-GFP and GAPDH, the latter being a control for a protein restricted to the intracellular environment. Cell surface biotinylation of FGF2-GFP was analyzed under various experimental conditions comparing a mock control with a titration (10, 25 and 50 μM) of both active (#6, #14 and #21) and inactive (#18 and #19) compounds (FIG. 8). Under these conditions, cell surface signals for FGF2-GFP were quantified using the LI-COR imaging platform. This analysis revealed all active compounds identified in the experiments shown in FIGS. 5, 6 and 7 to significantly inhibit FGF2 secretion from cells (FIGS. 8A, 8B and 8C). For compounds #6 and #14, inhibition was observed in a dose-dependent manner. In case of the active compound #21, inhibition was stronger at 10 μM compared to higher concentrations. This observation might be related to solubility issues since aggregates of compound #21 were increasingly observable at concentrations of 25 and 50 μM (data not shown). Importantly, the inactive compounds #18 and #19 did not affect FGF2 secretion from cells (FIGS. 8D and 8E). In addition, neither the active nor the inactive compounds exerted substantial pleiotropic effects on cell proliferation (FIG. 9). Using an IncuCyte Zoom live cell imaging platform, cell proliferation was quantified under mock conditions as well as in the presence of active and inactive compounds. While a modest decrease of cell proliferation could be observed, cells were viable and continued to proliferate under all experimental conditions as indicated (FIG. 9). These combined findings establish the active compounds #6, #14 and #21 as potent and selective inhibitors of Tec kinase mediated tyrosine phosphorylation (FIGS. 5, 6 and 7) that are also functional in a cellular context inhibiting FGF2 secretion (FIGS. 8 and 9).

DISCUSSION

The unconventional mechanism by which FGF2 is secreted from tumor cells has been worked out in considerable detail. FGF2 exits cells by direct translocation across the plasma membrane. This process involves (i) membrane recruitment at the inner leaflet mediated by the phosphoinositide PI $(4,5)P_2$, (ii) FGF2 oligomerization and membrane pore formation and (iii) extracellular trapping mediated by membrane-proximal heparan sulfate proteoglycans. In addition, Tec kinase and ATP1A1, two additional factors physically associated with the plasma membrane, have been shown to play critical roles in the unconventional secretory pathway of FGF2. While ATP1A1 is an integral membrane protein, Tec kinase contains a PH domain and associates with the inner leaflet via recruitment by the phosphoinositide PI $(3,4,5)P_3$. The precise role of ATP1A1 in unconventional secretion of FGF2 is unknown. By contrast, Tec kinase was shown to directly interact and phosphorylate FGF2, an activity causing increased membrane pore formation by FGF2 oligomers.

In the current study, based upon the stimulatory function of Tec kinase in unconventional secretion of FGF2, it was aimed at the identification of small molecule inhibitors that prevent Tec kinase from binding to FGF2. In turn, such compounds were rationalized to cause a failure of efficient tyrosine phosphorylation of FGF2 along with inhibition of FGF2 secretion from cells. A scaffold-based library of 79,000 small molecules was screened for protein-protein interaction inhibitors using Alpha® technology. Following primary screening, hits were reevaluated by determining dose-response curves focusing on compounds with IC50 values below 100 μM. Beyond the protein-protein interaction assays, inhibitors were further characterized by their potential to block Tec kinase mediated tyrosine phosphorylation of FGF2. The combination of these secondary assays revealed three active compounds characterized by IC50 values in the low μM range (7 μM, 9 μM and 12 μM, respectively) along with two structurally related compounds that were found inactive under all conditions. Beyond inhibition of FGF2 tyrosine phosphorylation, the active compounds also inhibited Tec kinase auto-phosphorylation. This was observed both in the presence and absence of FGF2, i.e., the active compounds affect Tec kinase even in the absence of a substrate. Intriguingly, tyrosine phosphorylation of a different substrate of Tec, STAP1, was unaffected in the presence of the active compounds. Moreover, Tec auto-phosphorylation was also unaffected under these conditions. These findings suggest that the active compounds prevent FGF2 tyrosine phosphorylation by blocking recruitment of FGF2 and inhibition of Tec auto-phosphorylation. However, in the presence of an unrelated substrate, the active compounds appear to get displaced from Tec kinase resulting in normal autophosphorylation of the enzyme and normal substrate phosphorylation.

Beyond the biochemical reconstitution experiments, it was also tested whether compounds blocking Tec mediated phosphorylation of FGF2 do affect FGF2 secretion from cells. While inhibition of FGF2 transport to the cell surface was not complete, all three active compounds exerted partial inhibition of FGF2 secretion of up to 50% in a statistically significant manner. While compounds #6 and #14 did so in a dose-dependent manner, compound #21 showed robust inhibition at 10 μM and somewhat less efficient inhibition at 25 and 50 μM, respectively. The latter observation may be due to solubility issues that were observed for compound #21 at higher concentrations in the context of cell culture media. In contrast to compounds #6, #14 and #21, the structurally related but inactive control compounds (#18 and #19) did not affect FGF2 secretion from cells. None of the compounds did affect general cell viability as measured by proliferation efficiencies. These findings suggest that, in a cellular context, the family of structurally related compounds described in this study does not cause pleiotropic effects to a significant extent.

Although the limited number of active compounds described in this study is insufficient to establish a full structure-activity relationship, there is clear guidance on how to proceed in subsequent chemical synthesis. These preliminary findings include (i) substitutions at the pyrrole moiety are tolerable, (ii) replacement of ester linkages is tolerated under some circumstances and (iii) re-scaffolding of the pyrido-pyrimidone scaffold is possible. Based on these modifications, defined pairs of compounds will be synthesized in future studies, a strategy that will allow for a clean determination of the structure-activity relationship of the Tec kinase inhibitors described in this work. These efforts will also aim at derivatives characterized by improved IC50 values along with systematic improvement of the balance between water solubility and membrane permeability to target the Tec/FGF2 complex inside cells.

In conclusion, the structures of the first inhibitors that have been specifically developed to block an unconventional secretory mechanism are reported. The present findings establish the identified small molecules as useful lead compounds for the development of further Tec kinase inhibitors with drug-like properties. Such drugs carry great potential to prevent the action of FGF2 as a tumor cell survival factor with non-small cell lung cancers being a prominent example. However, such inhibitors might have an even broader impact as cancer cells are characterized by strong overexpression of PI-3 kinases, the enzymes synthesizing $PI(3,4,5)P_3$. Since Tec kinases are recruited to the inner leaflet via $PI(3,4,5)P_3$ and FGF2 is highly overexpressed in many tumors, drugs preventing Tec-mediated tyrosine phosphorylation of FGF2 carry great potential for cancer therapy. Beyond their biomedical implications as lead compounds for drug development, the identified small molecule inhibitors corroborate the role of Tec kinase as a stimulatory component of the unconventional secretory pathway of FGF2. They further represent useful tool compounds to study the mechanism of unconventional secretory processes in general, in particular with regard to other cargoes such as HIV-Tat (43).

ABBREVIATIONS

CARP Cardiac adriamycin-responsive protein

EZ-Link Sulfo-NHS-SS-Biotin sulfosuccinimidyl-2-[biotinamido]ethyl-1,3-dithiopropionate FGF2 Fibroblast growth factor 2

HIV-Tat Human immunodeficiency virus trans-activator of transcription

IL1β Interleukin1β

MBP Maltose binding protein

NLS Nuclear localization signal

PH domain Pleckstrin homology domain $PI(4,5)P_2$ Phosphatidylinositol-4,5-bisphosphate STAP1 Signal transducing adaptor protein 1

TCEP Tris (2-carboxyethyl) phosphine hydrochloride

The invention claimed is:

1. A method for treating a cancerous or inflammatory disease in a human, comprising administering to the human a compound according to Formula (I) to treat the cancerous or inflammatory disease:

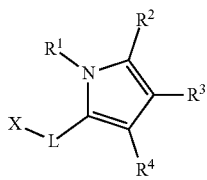
(I)

wherein
$R^1$ is H,
$R^2$ and $R^4$ are methyl,
$R^3$ is $C(O)CH_3$ or $C(O)OCH_3$,
L is —C(O)OCH$_2$— or —C(O)CH$_2$S—, and
X is selected from the group consisting of

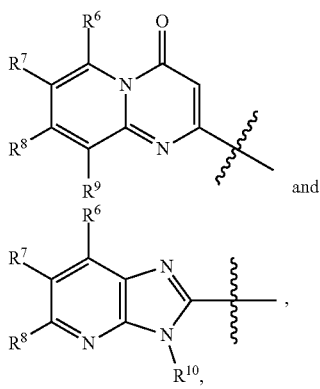

wherein
$R^6$, $R^7$, $R^8$ and $R^9$ are independently H, halogen, $C_1$-$C_3$ alkyl, —CN, —CF$_3$, OR$^{11}$ or Ar, and
$R^{10}$ and $R^{11}$ are independently H or $C_1$-$C_3$ alkyl.

2. The method of claim 1, wherein X is selected from the group consisting of

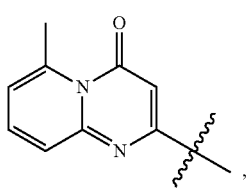

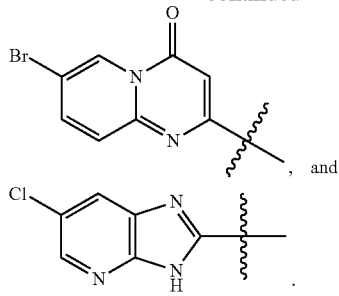

3. The method of claim 1 which compound according to Formula (I) is selected from the group consisting of (Compound 6)
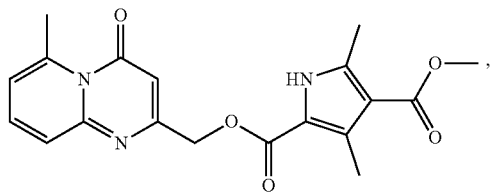

(Compound 14)
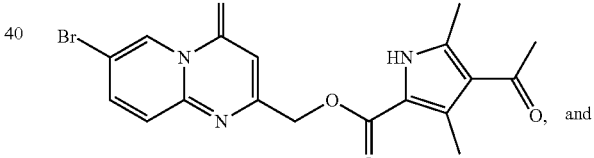

(Compound 21)
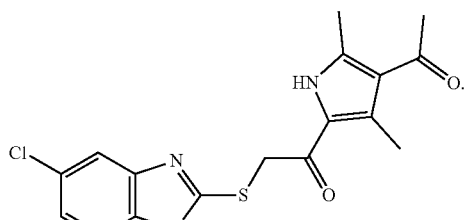

4. The method according to claim 1, wherein the method is for treating a cancerous disease.

5. The method according to claim 4, wherein VEGF-mediated signaling occurs in tumor cells of the cancer.

6. The method according to claim 1, wherein the method is for treating an inflammatory disease.

7. The method according to claim 6, wherein the method is for treating rheumatoid arthritis.

8. The method according to claim 3, which compound according to Formula (I) is (Compound 6)
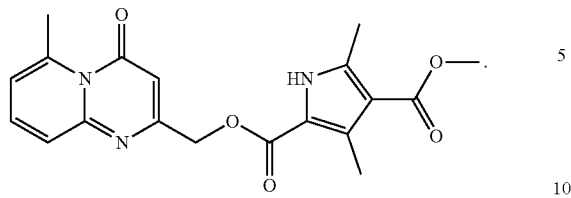
9. The method according to claim 1, wherein the method is for treating non-small cell lung cancer.
* * * * *

SEQUENCE LISTING

```
<160> NUMBER OF SEQ ID NOS: 2

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence:
      FGF2-derived synthetic peptide containing a phosphorylated
      tyrosine residue
<220> FEATURE:
<221> NAME/KEY: MOD_RES
<222> LOCATION: (4)..(4)
<223> OTHER INFORMATION: Phospho-Tyr

<400> SEQUENCE: 1

Ala Asn Arg Tyr Leu Ala Met Lys Glu Asp
1               5                   10

<210> SEQ ID NO 2
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      6xHis tag

<400> SEQUENCE: 2

His His His His His His
1               5
```